US012371495B2

(12) United States Patent
Shibuya et al.

(10) Patent No.: US 12,371,495 B2
(45) **Date of Patent: *Jul. 29, 2025**

(54) HUMANIZED ANTI-DNAM-1 ANTIBODY

(71) Applicants: University of Tsukuba, Tsukuba (JP); TNAX Biopharma Corporation, Tsukuba (JP)

(72) Inventors: Akira Shibuya, Tsukuba (JP); Kazuko Shibuya, Tsukuba (JP); Yumi Kanemaru, Cambridge (GB); Fumie Abe, Tsukuba (JP)

(73) Assignees: University of Tsukuba, Tsukuba (JP); TNAX Biopharma Corporation, Tsukuba (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/910,549

(22) Filed: Oct. 9, 2024

(65) Prior Publication Data

US 2025/0051442 A1 Feb. 13, 2025

Related U.S. Application Data

(63) Continuation of application No. 18/717,538, filed as application No. PCT/JP2021/046786 on Dec. 17, 2021.

(51) Int. Cl.
*C07K 16/28* (2006.01)
*C12N 15/63* (2006.01)

(52) U.S. Cl.
CPC .......... *C07K 16/2803* (2013.01); *C12N 15/63* (2013.01); *C07K 2317/24* (2013.01); *C07K 2317/565* (2013.01); *C07K 2317/71* (2013.01)

(58) Field of Classification Search
None
See application file for complete search history.

(56) References Cited

U.S. PATENT DOCUMENTS

| | | | | |
|---|---|---|---|---|
| 7,700,739 | B2 * | 4/2010 | Lacy ....................... | A61P 37/08 424/130.1 |
| 11,059,888 | B2 | 7/2021 | Shibuya et al. | |
| 2014/0056890 | A1 | 2/2014 | Gurney et al. | |
| 2016/0152720 | A1 | 6/2016 | Kim et al. | |
| 2019/0127462 | A1 | 5/2019 | Shibuya et al. | |
| 2020/0399366 | A1 | 12/2020 | Grogan et al. | |
| 2021/0032700 | A1 | 2/2021 | O'Leary et al. | |
| 2024/0150455 | A1 * | 5/2024 | Du ......................... | A61K 40/11 |

FOREIGN PATENT DOCUMENTS

| | | | |
|---|---|---|---|
| WO | 2013140787 | A1 | 9/2013 |
| WO | 2017183665 | A1 | 10/2017 |

OTHER PUBLICATIONS

Burns, Gordon F. et al., "TLiSA 1, A Human T Lineage-Specific Activation Antigen Involved in the Differentiation of Cytotoxic T Lymptocytes and Anomalous Killer Cells From Their Precursors", J. Exp. Med, May 1985, pp. 1063-1078, vol. 161.
Dardalhon, Valerie et al., "CD226 Is Specifically Expressed on the Surface of Th1 Cells and Regulates Their Expansion and Effector Functions", J. Immonol, 2004, pp. 1558-1565, vol. 175, No. 3.
Gilfillan, Susan et al., "DNAM-1 promotes activation of cytotoxic lymphocytes by nonprofessional antigen-presenting cells and tumors", J. Exp. Med., 2008, pp. 2965-2973, vol. 205, No. 13.
Sherrington, Paul D. et al., "TLiSA1 (PTA1) Activation Antigen Implicated in T Cell Differentiation and Platelet Activation Is a Member of the Immunoglobulin Superfamily Exhibiting Distinctive Regulation of Expression", The Journal of Biological Chemistry, Aug. 29, 1997, pp. 21735-21744, vol. 272, No. 35.
Shibuya, Akira et al., "DNAM-1, A Novel Adhesion Molecule Involved in the Cytolytic Function of T Lymphocytes", Immunity, Jun. 1996, pp. 573-581, vol. 4.
Shibuya, Kazuko et al., "Comment on 'CD226 Is Specifically Expressed on the Surface of Th1 Cells and Regulates Their Expansion and Effector Functions'", J Immunol, Apr. 1, 2006, pp. 3855-3857, vol. 176, No. 7.
Yamashita-Kanemaru, Yumi et al., "Suppression of Th1 and Th17 Proinflammatory Cytokines and Upregulation of FOXP3 Expression by a Humanized Anti-DNAM-1 Monoclonal Antibody", Monoclonal Antibodies in Immunodiagnosis and Immunotherapy, Nov. 2, 2021, vol. 40, No. 2.
Nabekura et al., "Type 1 Innate Lymphoid Cells Protect Mice from Acute Liver Injury via Interferon-γ Secretion for Upregulating Bcl-XL Expression in Hepatocytes", Immunity, Jan. 2020, pp. 96-108, vol. 52.

* cited by examiner

*Primary Examiner* — Daniel E Kolker
*Assistant Examiner* — James Ryland Melchior
(74) *Attorney, Agent, or Firm* — The Webb Law Firm

(57) ABSTRACT

One aspect of the present invention is a humanized anti-DNAM-1 antibody or an antigen-binding fragment thereof, including: a heavy chain variable region containing an amino acid sequence of SEQ ID NO: 1 as HCDR1, an amino acid sequence of SEQ ID NO: 2 as HCDR2, and an amino acid sequence of SEQ ID NO: 3 as HCDR3; and a light chain variable region containing an amino acid sequence of SEQ ID NO: 4 as LCDR1, an amino acid sequence of SEQ ID NO: 5 as LCDR2, and an amino acid sequence of SEQ ID NO: 6 as LCDR3.

21 Claims, 11 Drawing Sheets

Specification includes a Sequence Listing.

[Fig. 1]

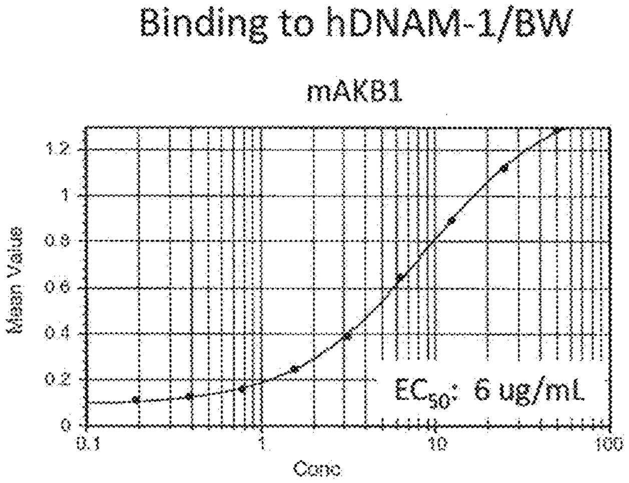

[Fig. 2]

```
COMPARISON OF HEAVY CHAIN VARIABLE REGIONS
                   1          2          3
            123456789 0123456789 0123456789 0123456789
mAKB1       DVQLQESGP GLVKPSQSLS LTCSVTGYSI TSGYYWNWIR
hAKB1 VH1   QVQLQESGP GLVKPSETLS LTCTVSGYSI TSGYYWNWIR
hAKB1 VH2   QVQLQESGP GLVKPSETLS LTCTVSGYSI SSGYYWNWIR
FJ039783 VH QVQLQESGP GLVKPSETLS LTCTVSGYSI S------WIR

                   4          5          6          7
            0123456789 0123456789 0123456789 0123456789
mAKB1       QFPGNKLEWM GYISYDGSNN YNPSLKNRIS ITRDTSKNQF
hAKB1 VH1   QPPGKGLEWM GYISYDGSNN YNPSLKNRVT ISRDTSKNQF
hAKB1 VH2   QPPGKGLEWM GYISYDGSNN YNPSLKNRVT ISRDTSKNQF
FJ039783 VH QPPGKGLEWI G--------- -------RVT ISVDTSKNQF

                                  1          1          1
                   8          9          0          1          2
            0123456789 0123456789 0123456789 0123456789 01
mAKB1       FLKLNSVTTE DTATYYCARA YYGNYVGYFD VWGAGTTVTV SS
hAKB1 VH1   SLKLSSVTAA DTAVYYCARA YYGNYVGYFD VWGQGTTVTV SS
hAKB1 VH2   SLKLSSVTAA DTAVYYCARA YYGNYVGYFD VWGQGTTVTV SS
FJ039783 VH SLKLSSVTAA DTAVYYCAR- ---------- -WGQGTTVTV SS
```

[Fig. 3]

COMPARISON OF LIGHT CHAIN VARIABLE REGIONS

```
                       1          2          3
              123456789 0123456789 0123456789 0123456789
mAKB1         SIVMTQTPK FLLVSAGDRV TITCKASQSV SNDVAWYQQK
hAKB1 VL1     DIQMTQSPS SLSASVGDRV TITCKASQSV SNDVAWYQQK
hAKB1 VL2     DIQMTQSPS SLSASVGDRV TITCKASQSV SNDVAWYQQK
KU760971 VL   DIQMTQSPS SLSASVGDRV TITC------ -----WYQQK

              4          5          6          7
              0123456789 0123456789 0123456789 0123456789
mAKB1         PGQSPKLLIY YASNRYTGVP DRFTGSGYGT DFTFTISTVQ
hAKB1 VL1     PGKAPKLLIY YASNRYTGVP SRFSGSGYGT DFTFTISSLQ
hAKB1 VL2     PGKAPKLLIY YASNRYTGVP SRFSGSGSGT DFTFTISSLQ
KU760971 VL   PGKAPKLLIY -------GVP SRFSGSGSGT DFTFTISSLQ

                                    1          1
              8          9          0          1
              0123456789 0123456789 0123456789 0
mAKB1         AEDLAVYFCQ QDYSSPLTFG AGTKLELKRT V
hAKB1 VL1     PEDIATYYCQ QDYSSPLTFG GGTKVEIKRT V
hAKB1 VL2     PEDIATYYCQ QDYSSPLTFG GGTKVEIKRT V
KU760971 VL   PEDIATYYC- --------FG GGTKVEIKRT V
```

[Fig. 4]
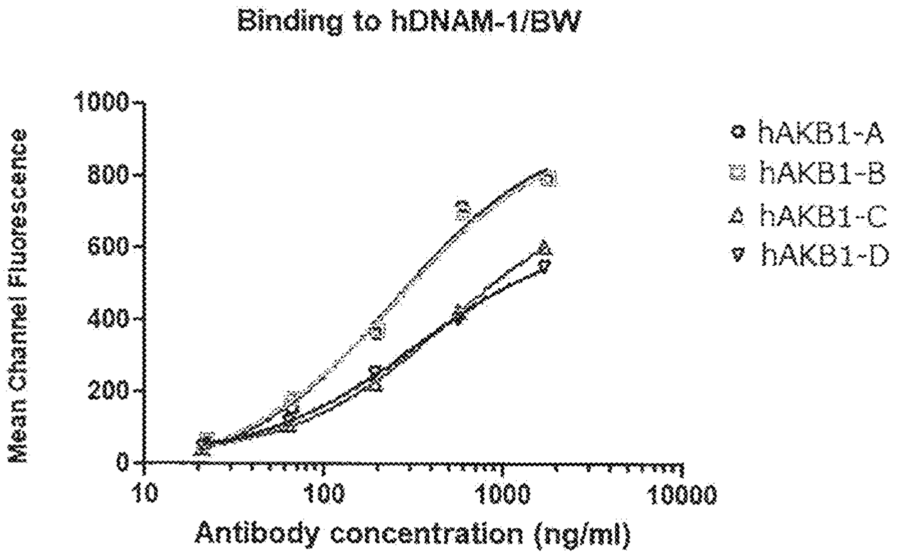
[Fig. 5]
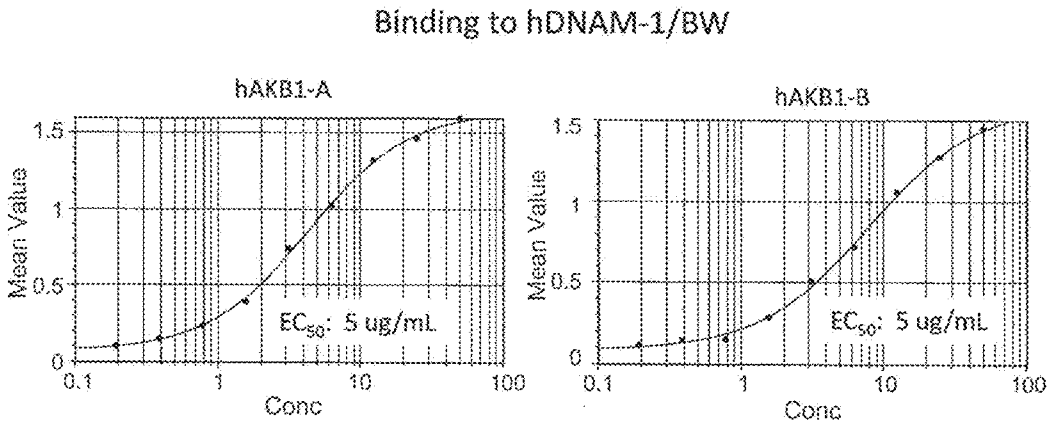

[Fig. 6]

BASE SEQUENCE (SEQ ID NO: 19) OF HEAVY CHAIN CODING REGION OF hAKB1-A

ATGAAAGTGTTGAGTCTGTTGTACCTGTTGACAGCCATTCCTGGTATCCTGTCTCAAGTTCAGCTTCAGG
AGTCAGGACCTGGCCTCGTGAAACCTTCTGAGACTCTGTCTCTCACCTGCACTGTCAGTGGCTACTCCAT
CACCAGTGGTTATTACTGGAACTGGATCCGGCAGCCTCCAGGAAAAGGACTGGAATGGATGGGCTACATC
AGCTACGACGGCAGCAATAACTACAACCCAAGTCTCAAGAATCGAGTCACCATCAGTCGTGACACATCTA
AGAACCAGTTTTCCCTGAAGTTGAGTTCTGTGACTGCTGCCGACACAGCTGTGTATTACTGTGCAAGGGC
CTACTATGGGAACTATGTGGCTACTTCGATGTCTGGGGCCAAGGGACCACTGTCACCGTCTCCTCAGCC
TCCACCAAGGGCCCATCGGTCTTCCCCCTGGCACCCTCCTCCAAGAGCACCTCTGGGGGCACAGCGGCCC
TGGGCTGCCTGGTCAAGGACTACTTCCCCGAACCGGTGACGGTGTCGTGGAACTCAGGCGCCCTGACCAG
CGGCGTGCACACCTTCCCGGCTGTCCTACAGTCCTCAGGACTCTACTCCCTCAGCAGCGTGGTGACCGTG
CCCTCCAGCAGCTTGGGCACCCAGACCTACATCTGCAACGTGAATCACAAGCCCAGCAACACCAAGGTGG
ACAAGAAAGTTGAGCCCAAATCTTGTGACAAAACTCACACATGCCCACCGTGCCCAGCACCTGAAGCTGC
TGGAGGACCGTCAGTCTTCCTCTTCCCCCCAAAACCCAAGGACACCCTCATGATCTCCCGGACCCCTGAG
GTCACATGCGTGGTGGTGGACGTGAGCCACGAAGACCCTGAGGTCAAGTTCAACTGGTACGTGGACGGCG
TGGAGGTGCATAATGCCAAGACAAAGCCGCGGGAGGAGCAGTACAACAGCACGTACCGTGTGGTCAGCGT
CCTCACCGTCCTGCACCAGGACTGGCTGAATGGCAAGGAGTACAAGTGCAAGGTCTCCAACAAAGCCCTC
CCAGCCCCCATCGAGAAAACCATCTCCAAAGCCAAAGGGCAGCCCCGAGAACCACAGGTGTACACCCTGC
CCCCATCCCGGGATGAGCTGACCAAGAACCAGGTCAGCCTGACCTGCCTGGTCAAAGGCTTCTATCCCAG
CGACATCGCCGTGGAGTGGGAGAGCAATGGGCAGCCGGAGAACAACTACAAGACCACGCCTCCCGTGCTG
GACTCCGACGGCTCCTTCTTCCTCTACAGCAAGCTCACCGTGGACAAGAGCAGGTGGCAGCAGGGGAACG
TCTTCTCATGCTCCGTGATGCATGAGGCTCTGCACAACCACTACACGCAGAAGAGCCTCTCCCTGTCTCC
GGGTAAATGA

[Fig. 7]

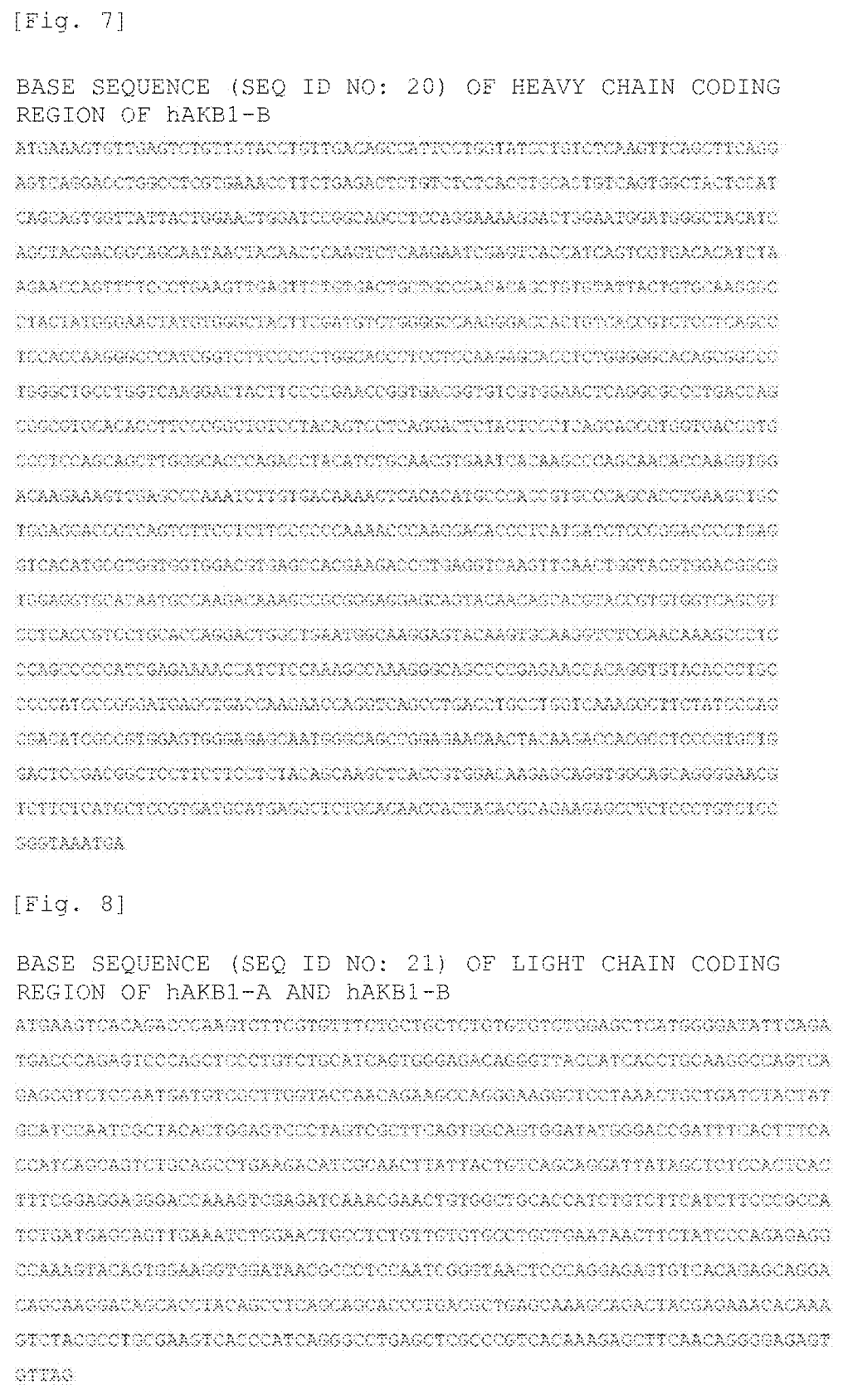

BASE SEQUENCE (SEQ ID NO: 20) OF HEAVY CHAIN CODING REGION OF hAKB1-B

ATGAAAGTGTTGAGTCTGTTGTACCTGTTGACAGCCATTCCTGGTATCCTGTCTCAAGTTCAGCTTCAGG
AGTCAGGACCTGGCCTCGTGAAACCTTCTGAGACTCTGTCTCTCACCTGCACTGTCAGTGGCTACTCCAT
CAGCAGTGGTTATTACTGGAACTGGATCCGGCAGCCTCCAGGAAAAGGACTGGAATGGATGGGCTACATC
AGCTACGACGGCAGCAATAACTACAACCCAAGTCTCAAGAATCGAGTCACCATCAGTCGTGACACATCTA
AGAACCAGTTTTCCCTGAAGTTGAGTTCTGTGACTGCTGCCGACACAGCTGTGTATTACTGTGCAAGGGC
CTACTATGGGAACTATGTGGGCTACTTCGATGTCTGGGGCCAAGGGACCACTGTCACCGTCTCCTCAGCC
TCCACCAAGGGCCCATCGGTCTTCCCCCTGGCACCCTCCTCCAAGAGCACCTCTGGGGGCACAGCGGCCC
TGGGCTGCCTGGTCAAGGACTACTTCCCCGAACCGGTGACGGTGTCGTGGAACTCAGGCGCCCTGACCAG
CGGCGTGCACACCTTCCCGGCTGTCCTACAGTCCTCAGGACTCTACTCCCTCAGCAGCGTGGTGACCGTG
CCCTCCAGCAGCTTGGGCACCCAGACCTACATCTGCAACGTGAATCACAAGCCCAGCAACACCAAGGTGG
ACAAGAAAGTTGAGCCCAAATCTTGTGACAAAACTCACACATGCCCACCGTGCCCAGCACCTGAAGCTGC
TGGAGGACCGTCAGTCTTCCTCTTCCCCCCAAAACCCAAGGACACCCTCATGATCTCCCGGACCCCTGAG
GTCACATGCGTGGTGGTGGACGTGAGCCACGAAGACCCTGAGGTCAAGTTCAACTGGTACGTGGACGGCG
TGGAGGTGCATAATGCCAAGACAAAGCCGCGGGAGGAGCAGTACAACAGCACGTACCGTGTGGTCAGCGT
CCTCACCGTCCTGCACCAGGACTGGCTGAATGGCAAGGAGTACAAGTGCAAGGTCTCCAACAAAGCCCTC
CCAGCCCCCATCGAGAAAACCATCTCCAAAGCCAAAGGGCAGCCCCGAGAACCACAGGTGTACACCCTGC
CCCCATCCCGGGATGAGCTGACCAAGAACCAGGTCAGCCTGACCTGCCTGGTCAAAGGCTTCTATCCCAG
CGACATCGCCGTGGAGTGGGAGAGCAATGGGCAGCCGGAGAACAACTACAAGACCACGCCTCCCGTGCTG
GACTCCGACGGCTCCTTCTTCCTCTACAGCAAGCTCACCGTGGACAAGAGCAGGTGGCAGCAGGGGAACG
TCTTCTCATGCTCCGTGATGCATGAGGCTCTGCACAACCACTACACGCAGAAGAGCCTCTCCCTGTCTCC
GGGTAAATGA

[Fig. 8]

BASE SEQUENCE (SEQ ID NO: 21) OF LIGHT CHAIN CODING REGION OF hAKB1-A AND hAKB1-B

ATGAAGTCACAGACCCAAGTCTTCGTGTTTCTGCTGCTCTGTGTGTCTGGAGCTCATGGGGATATTCAGA
TGACCCAGAGTCCCAGCTCCCTGTCTGCATCAGTGGGAGACAGGGTTACCATCACCTGCAAGGCCAGTCA
GAGCGTCTCCAATGATGTCGCTTGGTACCAACAGAAGCCAGGGAAGGCTCCTAAACTGCTGATCTACTAT
GCATCCAATCGCTACACTGGAGTCCCTAGTCGCTTCAGTGGCAGTGGATATGGGACCGATTTCACTTTCA
CCATCAGCAGTCTGCAGCCTGAAGACATCGCAACTTATTACTGTCAGCAGGATTATAGCTCTCCACTCAC
TTTCGGAGGAGGGACCAAAGTGGAGATCAAACGAACTGTGGCTGCACCATCTGTCTTCATCTTCCCGCCA
TCTGATGAGCAGTTGAAATCTGGAACTGCCTCTGTTGTGTGCCTGCTGAATAACTTCTATCCCAGAGAGG
CCAAAGTACAGTGGAAGGTGGATAACGCCCTCCAATCGGGTAACTCCCAGGAGAGTGTCACAGAGCAGGA
CAGCAAGGACAGCACCTACAGCCTCAGCAGCACCCTGACGCTGAGCAAAGCAGACTACGAGAAACACAAA
GTCTACGCCTGCGAAGTCACCCATCAGGGCCTGAGCTCGCCCGTCACAAAGAGCTTCAACAGGGGAGAGT
GTTAG

[Fig. 9]

AMINO ACID SEQUENCE (SEQ ID NO: 16) OF HEAVY CHAIN OF hAKB1-A

MKVLSLLYLLTAIPGILS**QVQLQESGPGLVKPSETLSLTCTVSGYSITSGYYWNWIRQP
PGKGLEWMGYISYDGSNNYNPSLKNRVTISRDTSKNQFSLKLSSVTAADTAVYYCARAY
YGNYVGYFDVWGQGTTVTVSS**ASTKGPSVFPLAPSSKSTSGGTAALGCLVKDYFPEPVT
VSWNSGALTSGVHTFPAVLQSSGLYSLSSVVTVPSSSLGTQTYICNVNHKPSNTKVDKK
VEPKSCDKTHTCPPCPAPEAAGGPSVFLFPPKPKDTLMISRTPEVTCVVVDVSHEDPEV
KFNWYVDGVEVHNAKTKPREEQYNSTYRVVSVLTVLHQDWLNGKEYKCKVSNKALPAPI
EKTISKAKGQPREPQVYTLPPSRDELTKNQVSLTCLVKGFYPSDIAVEWESNGQPENNY
KTTPPVLDSDGSFFLYSKLTVDKSRWQQGNVFSCSVMHEALHNHYTQKSLSLSPGK

AMINO ACID SEQUENCE (SEQ ID NO: 17) OF HEAVY CHAIN OF hAKB1-B

MKVLSLLYLLTAIPGILS**QVQLQESGPGLVKPSETLSLTCTVSGYSISSGYYWNWIRQP
PGKGLEWMGYISYDGSNNYNPSLKNRVTISRDTSKNQFSLKLSSVTAADTAVYYCARAY
YGNYVGYFDVWGQGTTVTVSS**ASTKGPSVFPLAPSSKSTSGGTAALGCLVKDYFPEPVT
VSWNSGALTSGVHTFPAVLQSSGLYSLSSVVTVPSSSLGTQTYICNVNHKPSNTKVDKK
VEPKSCDKTHTCPPCPAPEAAGGPSVFLFPPKPKDTLMISRTPEVTCVVVDVSHEDPEV
KFNWYVDGVEVHNAKTKPREEQYNSTYRVVSVLTVLHQDWLNGKEYKCKVSNKALPAPI
EKTISKAKGQPREPQVYTLPPSRDELTKNQVSLTCLVKGFYPSDIAVEWESNGQPENNY
KTTPPVLDSDGSFFLYSKLTVDKSRWQQGNVFSCSVMHEALHNHYTQKSLSLSPGK

AMINO ACID SEQUENCE (SEQ ID NO: 18) OF LIGHT CHAIN OF hAKB1-A AND hAKB1-B

MKSQTQVFVFLLLCVSGAHG**DIQMTQSPSSLSASVGDRVTITCKASQSVSNDVAWYQQK
PGKAPKLLIYYASNRYTGVPSRFSGSGYGTDFTFTISSLQPEDIATYYCQQDYSSPLTF
GGGTKVEIKRTV**AAPSVFIFPPSDEQLKSGTASVVCLLNNFYPREAKVQWKVDNALQSG
NSQESVTEQDSKDSTYSLSSTLTLSKADYEKHKVYACEVTHQGLSSPVTKSFNRGEC bold; variable region white text; signal peptide underline;CDRs

[Fig. 10]

BASE SEQUENCE (SEQ ID NO: 26) OF HEAVY CHAIN CODING REGION OF hTKB1

ATGAAACACCTGTGGTTCTTCCTCCTGCTGGTGGCAGCTCCCAGATGGGTCCTGTCCCAAGTTCAGCTGC

AAGAATCCGGACCCGGACTGGTGAAGCCCTCCGAGACTTTATCTTTAACTTGTACCGTGAGCGGCTACTC

CATCTCCTCCGGCTACTACTGGAACTGGATTCGTCAGCCTCCCGGCAAGGGTTTAGAATGGATGGGCTAC

ATCTCCTACGACGGCTCCAACAACTACAACCCCTCTTTAAAGAATCGTGTGACCATCTCTCGTGACACCT

CCAAGAACCAGTTCTCTTTAAAGCTGTCCTCCGTGACAGCCGCCGATACCGCCGTGTACTACTGCGCTCG

TGCCTACTACGGCAACTACGTGGGCTACTTCGACGTGTGGGGCCAAGGTACCACCGTGACAGTCTCCTCC

GCTAGCACCAAGGGCCCATCGGTCTTCCCCCTGGCACCCTCCTCCAAGAGCACCTCTGGGGGCACAGCGG

CCCTGGGCTGCCTGGTCAAGGACTACTTCCCCGAACCGGTGACGGTGTCGTGGAACTCAGGCGCCCTGAC

CAGCGGCGTGCACACCTTCCCGGCCGTCCTACAGTCCTCAGGACTCTACTCCCTCAGCAGCGTGGTGACC

GTGCCCTCCAGCAGCTTGGGCACCCAGACCTACATCTGCAACGTGAATCACAAGCCCAGCAACACCAAGG

TGGACAAGAAGGTTGAGCCCAAATCTTGTGACAAAACTCACACATGCCCACCGTGCCCAGCACCTGAAGC

AGCCGGGGGACCGTCAGTCTTCCTCTTCCCCCCAAAACCCAAGGACACCCTCATGATCTCCCGGACCCCT

GAGGTCACATGCGTGGTGGTGGACGTGAGCCACGAAGACCCTGAGGTCAAGTTCAACTGGTACGTGGACG

GCGTGGAGGTGCATAATGCCAAGACAAAGCCGCGGGAGGAGCAGTACAACAGCACGTACCGTGTGGTCAG

CGTCCTCACCGTCCTGCACCAGGACTGGCTGAATGGCAAGGAGTACAAGTGCAAGGTCTCCAACAAAGCC

CTCCCAGCCCCCATCGAGAAAACCATCTCCAAAGCCAAAGGGCAGCCCCGAGAACCACAGGTGTACACCC

TGCCCCCATCCCGGGACGAGCTGACCAAGAACCAGGTCAGCCTGACCTGCCTGGTCAAAGGCTTCTATCC

CAGCGACATCGCCGTGGAGTGGGAGAGCAATGGGCAGCCGGAGAACAACTACAAGACCACGCCTCCCGTG

CTGGACTCCGACGGCTCCTTCTTCCTCTACAGCAAGCTCACCGTGGACAAGAGCAGGTGGCAGCAGGGGA

ACGTCTTCTCATGCTCCGTGATGCATGAGGCTCTGCACAACCACTACACGCAGAAGAGCCTCTCCCTGTC

TCCGGGTAAATGATGA bold; variable region white text; signal peptide

[Fig. 11]

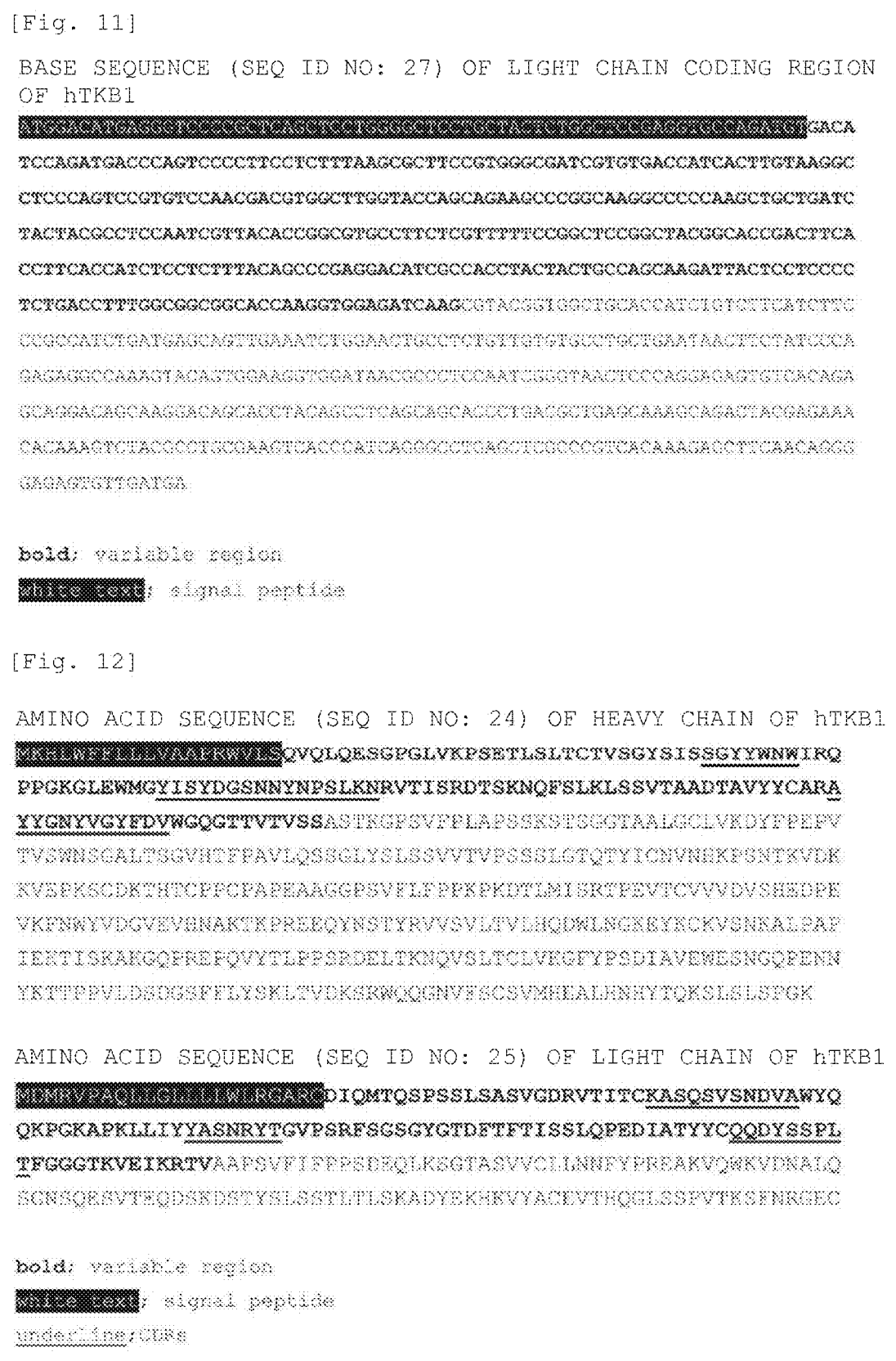

BASE SEQUENCE (SEQ ID NO: 27) OF LIGHT CHAIN CODING REGION OF hTKB1

[illegible]GACA
TCCAGATGACCCAGTCCCCTTCCTCTTTAAGCGCTTCCGTGGGCGATCGTGTGACCATCACTTGTAAGGC
CTCCCAGTCCGTGTCCAACGACGTGGCTTGGTACCAGCAGAAGCCCGGCAAGGCCCCCAAGCTGCTGATC
TACTACGCCTCCAATCGTTACACCGGCGTGCCTTCTCGTTTTTCCGGCTCCGGCTACGGCACCGACTTCA
CCTTCACCATCTCCTCTTTACAGCCCGAGGACATCGCCACCTACTACTGCCAGCAAGATTACTCCTCCCC
TCTGACCTTTGGCGGCGGCACCAAGGTGGAGATCAAGCGTACGGTGGCTGCACCATCTGTCTTCATCTTC
CCGCCATCTGATGAGCAGTTGAAATCTGGAACTGCCTCTGTTGTGTGCCTGCTGAATAACTTCTATCCCA
GAGAGGCCAAAGTACAGTGGAAGGTGGATAACGCCCTCCAATCGGGTAACTCCCAGGAGAGTGTCACAGA
GCAGGACAGCAAGGACAGCACCTACAGCCTCAGCAGCACCCTGACGCTGAGCAAAGCAGACTACGAGAAA
CACAAAGTCTACGCCTGCGAAGTCACCCATCAGGGCCTGAGCTCGCCCGTCACAAAGAGCTTCAACAGGG
GAGAGTGTTGATGA bold; variable region white text; signal peptide

[Fig. 12]

AMINO ACID SEQUENCE (SEQ ID NO: 24) OF HEAVY CHAIN OF hTKB1

MKHLWFFLLLVAAPRWVLSQVQLQESGPGLVKPSETLSLTCTVSGYSISSGYYWNWIRQ
PPGKGLEWMGYISYDGSNNYNPSLKNRVTISRDTSKNQFSLKLSSVTAADTAVYYCARA
YYGNYVGYFDVWGQGTTVTVSSASTKGPSVFPLAPSSKSTSGGTAALGCLVKDYFPEPV
TVSWNSGALTSGVHTFPAVLQSSGLYSLSSVVTVPSSSLGTQTYICNVNHKPSNTKVDK
KVEPKSCDKTHTCPPCPAPEAAGGPSVFLFPPKPKDTLMISRTPEVTCVVVDVSHEDPE
VKFNWYVDGVEVHNAKTKPREEQYNSTYRVVSVLTVLHQDWLNGKEYKCKVSNKALPAP
IEKTISKAKGQPREPQVYTLPPSRDELTKNQVSLTCLVKGFYPSDIAVEWESNGQPENN
YKTTPPVLDSDGSFFLYSKLTVDKSRWQQGNVFSCSVMHEALHNHYTQKSLSLSPGK

AMINO ACID SEQUENCE (SEQ ID NO: 25) OF LIGHT CHAIN OF hTKB1

MDMRVPAQLLGLLLLWLRGARCDIQMTQSPSSLSASVGDRVTITCKASQSVSNDVAWYQ
QKPGKAPKLLIYYASNRYTGVPSRFSGSGYGTDFTFTISSLQPEDIATYYCQQDYSSPL
TFGGGTKVEIKRTVAAPSVFIFPPSDEQLKSGTASVVCLLNNFYPREAKVQWKVDNALQ
SGNSQESVTEQDSKDSTYSLSSTLTLSKADYEKHKVYACEVTHQGLSSPVTKSFNRGEC bold; variable region white text; signal peptide underline; CDRs

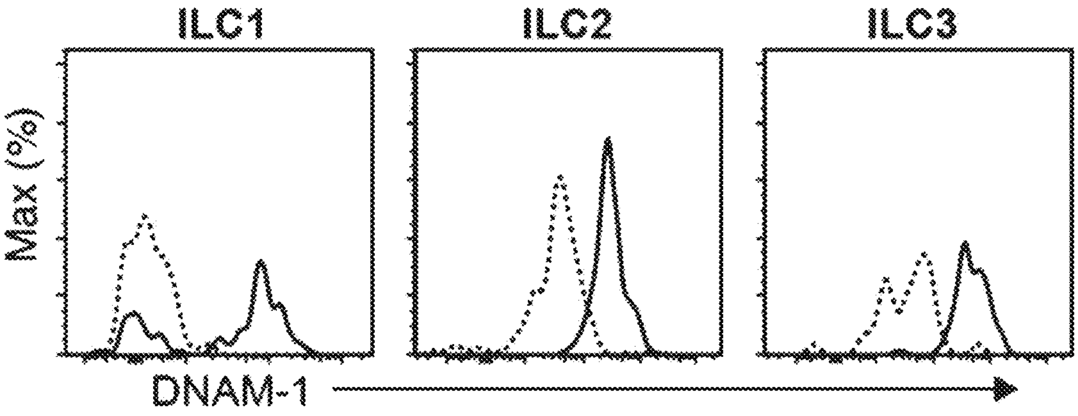
[Fig. 13B]
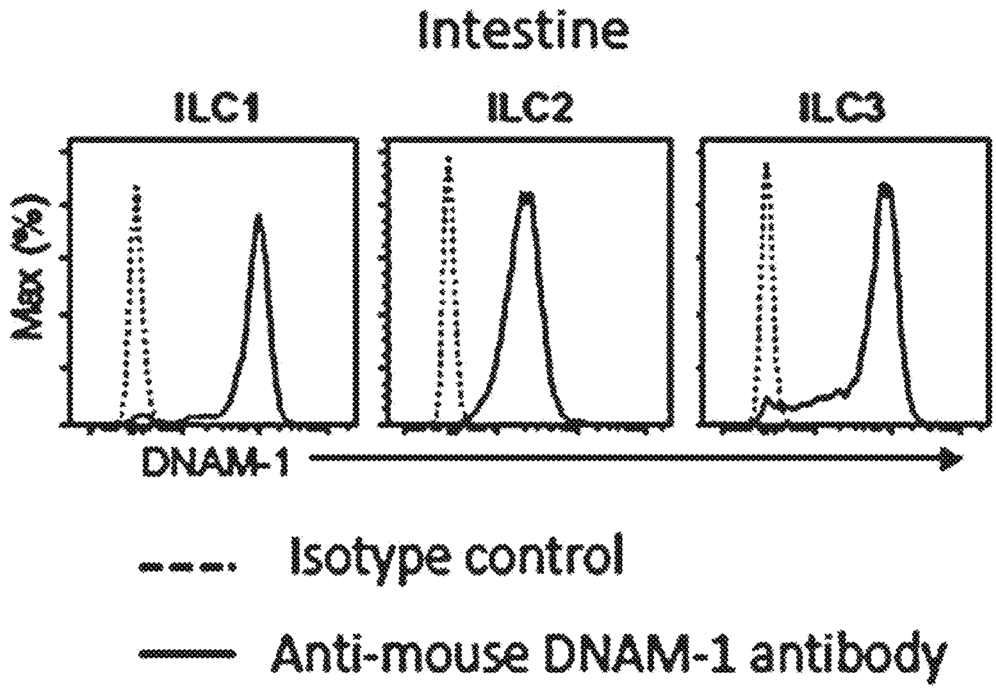

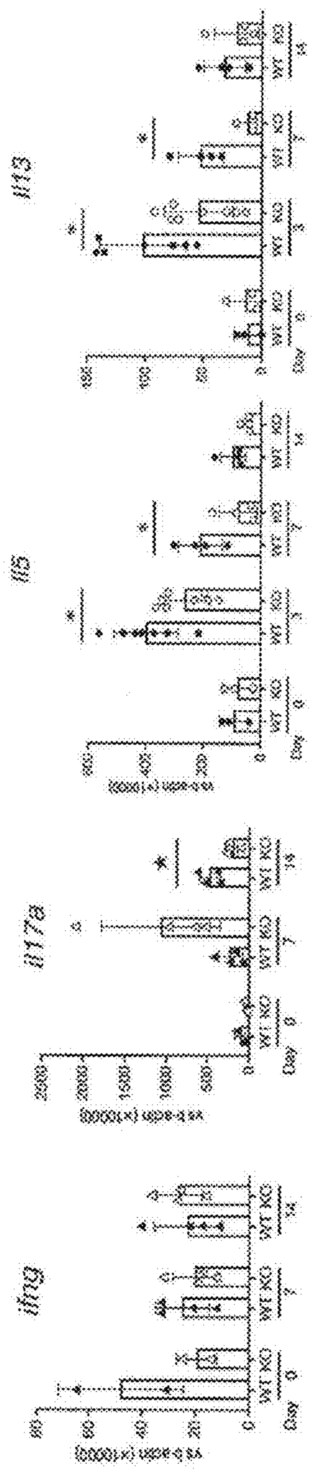
[FIG. 14]

[Fig. 15]
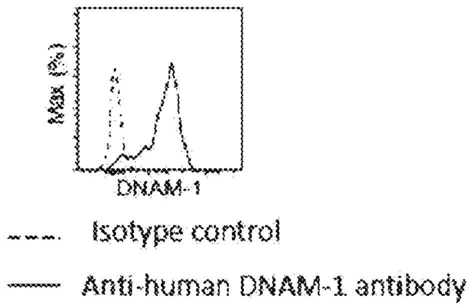
[Fig. 16]
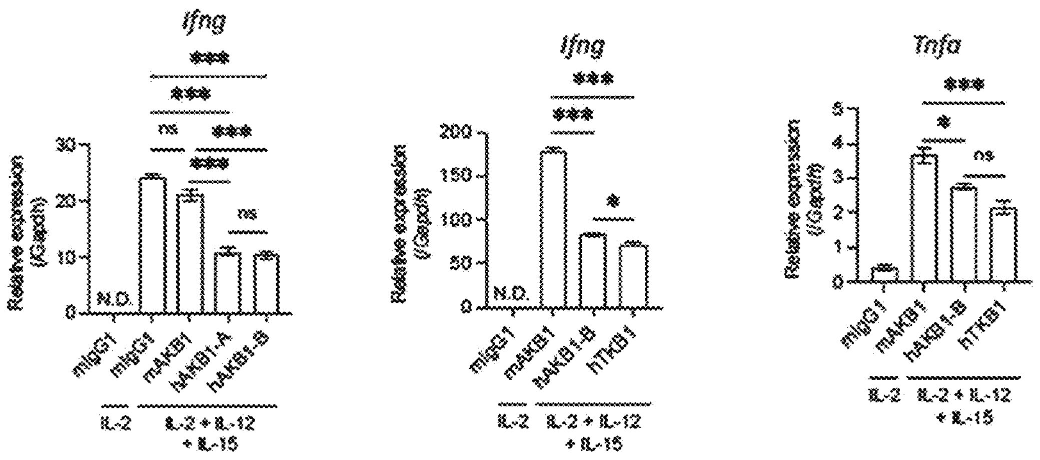

SEQUENCE LISTING

```
Sequence total quantity: 40
SEQ ID NO: 1            moltype = AA  length = 7
FEATURE                 Location/Qualifiers
REGION                  1..7
                        note = HCDR1 of hTKB1,hAKB1-A and hAKB1-B
source                  1..7
                        mol_type = protein
                        organism = synthetic construct
SEQUENCE: 1
SGYYWNW                                                              7

SEQ ID NO: 2            moltype = AA  length = 16
FEATURE                 Location/Qualifiers
REGION                  1..16
                        note = HCDR2 of hTKB1,hAKB1-A and hAKB1-B
source                  1..16
                        mol_type = protein
                        organism = synthetic construct
SEQUENCE: 2
YISYDGSNNY NPSLKN                                                    16

SEQ ID NO: 3            moltype = AA  length = 12
FEATURE                 Location/Qualifiers
REGION                  1..12
                        note = HCDR3 of hTKB1,hAKB1-A and hAKB1-B
source                  1..12
                        mol_type = protein
                        organism = synthetic construct
SEQUENCE: 3
AYYGNYVGYF DV                                                        12

SEQ ID NO: 4            moltype = AA  length = 11
FEATURE                 Location/Qualifiers
REGION                  1..11
                        note = LCDR1 of hTKB1,hAKB1-A and hAKB1-B
source                  1..11
                        mol_type = protein
                        organism = synthetic construct
SEQUENCE: 4
KASQSVSNDV A                                                         11

SEQ ID NO: 5            moltype = AA  length = 7
FEATURE                 Location/Qualifiers
REGION                  1..7
                        note = LCDR2 of hTKB1,hAKB1-A and hAKB1-B
source                  1..7
                        mol_type = protein
                        organism = synthetic construct
SEQUENCE: 5
YASNRYT                                                              7
```

-continued

```
SEQ ID NO: 6            moltype = AA  length = 9
FEATURE                 Location/Qualifiers
REGION                  1..9
                        note = LCDR3 of hTKB1,hAKB1-A and hAKB1-B
source                  1..9
                        mol_type = protein
                        organism = synthetic construct
SEQUENCE: 6
QQDYSSPLT                                                          9

SEQ ID NO: 7            moltype = AA  length = 121
FEATURE                 Location/Qualifiers
source                  1..121
                        mol_type = protein
                        organism = Mus musculus
SEQUENCE: 7
DVQLQESGPG LVKPSQSLSL TCSVTGYSIT SGYYWNWIRQ FPGNKLEWMG YISYDGSNNY  60
NPSLKNRISI TRDTSKNQFF LKLNSVTTED TATYYCARAY YGNYVGYFDV WGAGTTVTVS  120
S                                                                  121

SEQ ID NO: 8            moltype = AA  length = 110
FEATURE                 Location/Qualifiers
source                  1..110
                        mol_type = protein
                        organism = Mus musculus
SEQUENCE: 8
SIVMTQTPKF LLVSAGDRVT ITCKASQSVS NDVAWYQQKP GQSPKLLIYY ASNRYTGVPD  60
RFTGSGYGTD FTFTISTVQA EDLAVYFCQQ DYSSPLTFGA GTKLELKRTV             110

SEQ ID NO: 9            moltype = AA  length = 121
FEATURE                 Location/Qualifiers
REGION                  1..121
                        note = heavy chain variable region of hAKB1 VH1
source                  1..121
                        mol_type = protein
                        organism = synthetic construct
SEQUENCE: 9
QVQLQESGPG LVKPSETLSL TCTVSGYSIT SGYYWNWIRQ PPGKGLEWMG YISYDGSNNY  60
NPSLKNRVTI SRDTSKNQFS LKLSSVTAAD TAVYYCARAY YGNYVGYFDV WGQGTTVTVS  120
S                                                                  121

SEQ ID NO: 10           moltype = AA  length = 121
FEATURE                 Location/Qualifiers
REGION                  1..121
                        note = heavy chain variable region of hAKB1 VH2
source                  1..121
                        mol_type = protein
                        organism = synthetic construct
SEQUENCE: 10
QVQLQESGPG LVKPSETLSL TCTVSGYSIS SGYYWNWIRQ PPGKGLEWMG YISYDGSNNY  60
NPSLKNRVTI SRDTSKNQFS LKLSSVTAAD TAVYYCARAY YGNYVGYFDV WGQGTTVTVS  120
S                                                                  121

SEQ ID NO: 11           moltype = AA  length = 110
FEATURE                 Location/Qualifiers
REGION                  1..110
                        note = light chain variable region of hAKB1 VL1
source                  1..110
                        mol_type = protein
                        organism = synthetic construct
SEQUENCE: 11
DIQMTQSPSS LSASVGDRVT ITCKASQSVS NDVAWYQQKP GKAPKLLIYY ASNRYTGVPS  60
RFSGSGYGTD FTFTISSLQP EDIATYYCQQ DYSSPLTFGG GTKVEIKRTV             110

SEQ ID NO: 12           moltype = AA  length = 110
FEATURE                 Location/Qualifiers
REGION                  1..110
                        note = light chain variable region of hAKB1 VL2
source                  1..110
                        mol_type = protein
                        organism = synthetic construct
SEQUENCE: 12
DIQMTQSPSS LSASVGDRVT ITCKASQSVS NDVAWYQQKP GKAPKLLIYY ASNRYTGVPS  60
RFSGSGSGTD FTFTISSLQP EDIATYYCQQ DYSSPLTFGG GTKVEIKRTV             110

SEQ ID NO: 13           moltype = AA  length = 451
FEATURE                 Location/Qualifiers
REGION                  1..451
                        note = heavy chain of hAKB1-A without signal peptide
```

-continued

```
source                1..451
                      mol_type = protein
                      organism = synthetic construct
SEQUENCE: 13
QVQLQESGPG LVKPSETLSL TCTVSGYSIT SGYYWNWIRQ PPGKGLEWMG YISYDGSNNY  60
NPSLKNRVTI SRDTSKNQFS LKLSSVTAAD TAVYYCARAY YGNYVGYFDV WGQGTTVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPEAAG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG K                                451

SEQ ID NO: 14         moltype = AA  length = 451
FEATURE               Location/Qualifiers
REGION                1..451
                      note = heavy chain of hAKB1-B without signal peptide
source                1..451
                      mol_type = protein
                      organism = synthetic construct
SEQUENCE: 14
QVQLQESGPG LVKPSETLSL TCTVSGYSIS SGYYWNWIRQ PPGKGLEWMG YISYDGSNNY  60
NPSLKNRVTI SRDTSKNQFS LKLSSVTAAD TAVYYCARAY YGNYVGYFDV WGQGTTVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPEAAG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG K                                451

SEQ ID NO: 15         moltype = AA  length = 214
FEATURE               Location/Qualifiers
REGION                1..214
                      note = light chain of hAKB1-A and hAKB1-B without signal
                       peptide
source                1..214
                      mol_type = protein
                      organism = synthetic construct
SEQUENCE: 15
DIQMTQSPSS LSASVGDRVT ITCKASQSVS NDVAWYQQKP GKAPKLLIYY ASNRYTGVPS  60
RFSGSGYGTD FTFTISSLQP EDIATYYCQQ DYSSPLTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 16         moltype = AA  length = 469
FEATURE               Location/Qualifiers
REGION                1..469
                      note = heavy chain of hAKB1-A with signal peptide
source                1..469
                      mol_type = protein
                      organism = synthetic construct
SEQUENCE: 16
MKVLSLLYLL TAIPGILSQV QLQESGPGLV KPSETLSLTC TVSGYSITSG YYWNWIRQPP  60
GKGLEWMGYI SYDGSNNYNP SLKNRVTISR DTSKNQFSLK LSSVTAADTA VYYCARAYYG  120
NYVGYFDVWG QGTTVTVSSA STKGPSVFPL APSSKSTSGG TAALGCLVKD YFPEPVTVSW  180
NSGALTSGVH TFPAVLQSSG LYSLSSVVTV PSSSLGTQTY ICNVNHKPSN TKVDKKVEPK  240
SCDKTHTCPP CPAPEAAGGP SVFLFPPKPK DTLMISRTPE VTCVVVDVSH EDPEVKFNWY  300
VDGVEVHNAK TKPREEQYNS TYRVVSVLTV LHQDWLNGKE YKCKVSNKAL PAPIEKTISK  360
AKGQPREPQV YTLPPSRDEL TKNQVSLTCL VKGFYPSDIA VEWESNGQPE NNYKTTPPVL  420
DSDGSFFLYS KLTVDKSRWQ QGNVFSCSVM HEALHNHYTQ KSLSLSPGK             469

SEQ ID NO: 17         moltype = AA  length = 469
FEATURE               Location/Qualifiers
REGION                1..469
                      note = heavy chain of hAKB1-B with signal peptide
source                1..469
                      mol_type = protein
                      organism = synthetic construct
SEQUENCE: 17
MKVLSLLYLL TAIPGILSQV QLQESGPGLV KPSETLSLTC TVSGYSISSG YYWNWIRQPP  60
GKGLEWMGYI SYDGSNNYNP SLKNRVTISR DTSKNQFSLK LSSVTAADTA VYYCARAYYG  120
NYVGYFDVWG QGTTVTVSSA STKGPSVFPL APSSKSTSGG TAALGCLVKD YFPEPVTVSW  180
NSGALTSGVH TFPAVLQSSG LYSLSSVVTV PSSSLGTQTY ICNVNHKPSN TKVDKKVEPK  240
SCDKTHTCPP CPAPEAAGGP SVFLFPPKPK DTLMISRTPE VTCVVVDVSH EDPEVKFNWY  300
VDGVEVHNAK TKPREEQYNS TYRVVSVLTV LHQDWLNGKE YKCKVSNKAL PAPIEKTISK  360
AKGQPREPQV YTLPPSRDEL TKNQVSLTCL VKGFYPSDIA VEWESNGQPE NNYKTTPPVL  420
DSDGSFFLYS KLTVDKSRWQ QGNVFSCSVM HEALHNHYTQ KSLSLSPGK             469

SEQ ID NO: 18         moltype = AA  length = 234
```

-continued

```
FEATURE                Location/Qualifiers
REGION                 1..234
                       note = light chain of hAKB1-A and hAKB1-B with signal
                        peptide
source                 1..234
                       mol_type = protein
                       organism = synthetic construct
SEQUENCE: 18
MKSQTQVFVF LLLCVSGAHG DIQMTQSPSS LSASVGDRVT ITCKASQSVS NDVAWYQQKP  60
GKAPKLLIYY ASNRYTGVPS RFSGSGYGTD FTFTISSLQP EDIATYYCQQ DYSSPLTFGG  120
GTKVEIKRTV AAPSVFIFPP SDEQLKSGTA SVVCLLNNFY PREAKVQWKV DNALQSGNSQ  180
ESVTEQDSKD STYSLSSTLT LSKADYEKHK VYACEVTHQG LSSPVTKSFN RGEC        234

SEQ ID NO: 19          moltype = DNA  length = 1410
FEATURE                Location/Qualifiers
misc_feature           1..1410
                       note = coding region of heavy chain of hAKB1-A
source                 1..1410
                       mol_type = other DNA
                       organism = synthetic construct
SEQUENCE: 19
atgaaagtgt tgagtctgtt gtacctgttg acagccattc ctggtatcct gtctcaagtt  60
cagcttcagg agtcaggacc tggcctcgtg aaaccttctg agactctgtc tctcacctgc  120
actgtcagtg gctactccat caccagtggt tattactgga actggatccg gcagcctcca  180
ggaaaaggac tggaatggat gggctacatc agctacgacg gcagcaataa ctacaaccca  240
agtctcaaga atcgagtcac catcagtcgt gacacatcta agaaccagtt ttccctgaag  300
ttgagttctg tgactgctgc cgacacagct gtgtattact gtgcaagggc ctactatggg  360
aactatgtgg gctacttcga tgtctggggc caagggacca ctgtcaccgt ctcctcagcc  420
tccaccaagg gcccatcggt cttccccctg gcaccctcct ccaagagcac ctctgggggc  480
acagcggccc tgggctgcct ggtcaaggac tacttccccg aaccggtgac ggtgtcgtgg  540
aactcaggcg ccctgaccag cggcgtgcac accttcccgg ctgtcctaca gtcctcagga  600
ctctactccc tcagcagcgt ggtgaccgtg ccctccagca gcttgggcac ccagacctac  660
atctgcaacg tgaatcacaa gcccagcaac accaaggtgg acaagaaagt tgagcccaaa  720
tcttgtgaca aaactcacac atgcccaccg tgcccagcac ctgaagctgc tggaggaccg  780
tcagtcttcc tcttcccccc aaaacccaag gacaccctca tgatctcccg gacccctgag  840
gtcacatgcg tggtggtgga cgtgagccac gaagaccctg aggtcaagtt caactggtac  900
gtggacggcg tggaggtgca taatgccaag acaaagccgc gggaggagca gtacaacagc  960
acgtaccgtg tggtcagcgt cctcaccgtc ctgcaccagg actggctgaa tggcaaggag  1020
tacaagtgca aggtctccaa caaagccctc ccagccccca tcgagaaaac catctccaaa  1080
gccaaagggc agccccgaga accacaggtg tacaccctgc ccccatcccg ggatgagctg  1140
accaagaacc aggtcagcct gacctgcctg gtcaaaggct tctatcccag cgacatcgcc  1200
gtggagtggg agagcaatgg gcagccggag aacaactaca agaccacgcc tcccgtgctg  1260
gactccgacg gctccttctt cctctacagc aagctcaccg tggacaagag caggtggcag  1320
caggggaacg tcttctcatg ctccgtgatg catgaggctc tgcacaacca ctacacgcag  1380
aagagcctct ccctgtctcc gggtaaatga                                  1410

SEQ ID NO: 20          moltype = DNA  length = 1410
FEATURE                Location/Qualifiers
misc_feature           1..1410
                       note = coding region of heavy chain of hAKB1-B
source                 1..1410
                       mol_type = other DNA
                       organism = synthetic construct
SEQUENCE: 20
atgaaagtgt tgagtctgtt gtacctgttg acagccattc ctggtatcct gtctcaagtt  60
cagcttcagg agtcaggacc tggcctcgtg aaaccttctg agactctgtc tctcacctgc  120
actgtcagtg gctactccat cagcagtggt tattactgga actggatccg gcagcctcca  180
ggaaaaggac tggaatggat gggctacatc agctacgacg gcagcaataa ctacaaccca  240
agtctcaaga atcgagtcac catcagtcgt gacacatcta agaaccagtt ttccctgaag  300
ttgagttctg tgactgctgc cgacacagct gtgtattact gtgcaagggc ctactatggg  360
aactatgtgg gctacttcga tgtctggggc caagggacca ctgtcaccgt ctcctcagcc  420
tccaccaagg gcccatcggt cttccccctg gcaccctcct ccaagagcac ctctgggggc  480
acagcggccc tgggctgcct ggtcaaggac tacttccccg aaccggtgac ggtgtcgtgg  540
aactcaggcg ccctgaccag cggcgtgcac accttcccgg ctgtcctaca gtcctcagga  600
ctctactccc tcagcagcgt ggtgaccgtg ccctccagca gcttgggcac ccagacctac  660
atctgcaacg tgaatcacaa gcccagcaac accaaggtgg acaagaaagt tgagcccaaa  720
tcttgtgaca aaactcacac atgcccaccg tgcccagcac ctgaagctgc tggaggaccg  780
tcagtcttcc tcttcccccc aaaacccaag gacaccctca tgatctcccg gacccctgag  840
gtcacatgcg tggtggtgga cgtgagccac gaagaccctg aggtcaagtt caactggtac  900
gtggacggcg tggaggtgca taatgccaag acaaagccgc gggaggagca gtacaacagc  960
acgtaccgtg tggtcagcgt cctcaccgtc ctgcaccagg actggctgaa tggcaaggag  1020
tacaagtgca aggtctccaa caaagccctc ccagccccca tcgagaaaac catctccaaa  1080
gccaaagggc agccccgaga accacaggtg tacaccctgc ccccatcccg ggatgagctg  1140
accaagaacc aggtcagcct gacctgcctg gtcaaaggct tctatcccag cgacatcgcc  1200
gtggagtggg agagcaatgg gcagccggag aacaactaca agaccacgcc tcccgtgctg  1260
gactccgacg gctccttctt cctctacagc aagctcaccg tggacaagag caggtggcag  1320
caggggaacg tcttctcatg ctccgtgatg catgaggctc tgcacaacca ctacacgcag  1380
aagagcctct ccctgtctcc gggtaaatga                                  1410
```

-continued

```
SEQ ID NO: 21          moltype = DNA  length = 705
FEATURE                Location/Qualifiers
misc_feature           1..705
                       note = coding region of light chain of hAKB1-A and hAKB1-B
source                 1..705
                       mol_type = other DNA
                       organism = synthetic construct
SEQUENCE: 21
atgaagtcac agacccaagt cttcgtgttt ctgctgctct gtgtgtctgg agctcatggg  60
gatattcaga tgacccagag tcccagctcc ctgtctgcat cagtgggaga cagggttacc  120
atcacctgca aggccagtca gagcgtctcc aatgatgtcg cttggtacca acagaagcca  180
gggaaggctc ctaaactgct gatctactat gcatccaatc gctacactgg agtccctagt  240
cgcttcagtg gcagtggata tgggaccgat ttcactttca ccatcagcag tctgcagcct  300
gaagacatcg caacttatta ctgtcagcag gattatagct ctccactcac tttcggagga  360
gggaccaaag tcgagatcaa acgaactgtg gctgcaccat ctgtcttcat cttcccgcca  420
tctgatgagc agttgaaatc tggaactgcc tctgttgtgt gcctgctgaa taacttctat  480
cccagagagg ccaaagtaca gtggaaggtg gataacgccc tccaatcggg taactcccag  540
gagagtgtca cagagcagga cagcaaggac agcacctaca gcctcagcag caccctgacg  600
ctgagcaaag cagactacga gaaacacaaa gtctacgcct gcgaagtcac ccatcagggc  660
ctgagctcgc ccgtcacaaa gagcttcaac aggggagagt gttag                705

SEQ ID NO: 22          moltype = AA  length = 451
FEATURE                Location/Qualifiers
REGION                 1..451
                       note = heavy chain of hTKB1 without signal peptide
source                 1..451
                       mol_type = protein
                       organism = synthetic construct
SEQUENCE: 22
QVQLQESGPG LVKPSETLSL TCTVSGYSIS SGYYWNWIRQ PPGKGLEWMG YISYDGSNNY  60
NPSLKNRVTI SRDTSKNQFS LKLSSVTAAD TAVYYCARAY YGNYVGYFDV WGQGTTVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPEAAG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG K                                451

SEQ ID NO: 23          moltype = AA  length = 214
FEATURE                Location/Qualifiers
REGION                 1..214
                       note = light chain of hTKB1 without signal peptide
source                 1..214
                       mol_type = protein
                       organism = synthetic construct
SEQUENCE: 23
DIQMTQSPSS LSASVGDRVT ITCKASQSVS NDVAWYQQKP GKAPKLLIYY ASNRYTGVPS  60
RFSGSGYGTD FTFTISSLQP EDIATYYCQQ DYSSPLTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 24          moltype = AA  length = 470
FEATURE                Location/Qualifiers
REGION                 1..470
                       note = heavy chain of hTKB1 with signal peptide
source                 1..470
                       mol_type = protein
                       organism = synthetic construct
SEQUENCE: 24
MKHLWFFLLL VAAPRWVLSQ VQLQESGPGL VKPSETLSLT CTVSGYSISS GYYWNWIRQP  60
PGKGLEWMGY ISYDGSNNYN PSLKNRVTIS RDTSKNQFSL KLSSVTAADT AVYYCARAYY  120
GNYVGYFDVW GQGTTVTVSS ASTKGPSVFP LAPSSKSTSG GTAALGCLVK DYFPEPVTVS  180
WNSGALTSGV HTFPAVLQSS GLYSLSSVVT VPSSSLGTQT YICNVNHKPS NTKVDKKVEP  240
KSCDKTHTCP PCPAPEAAGG PSVFLFPPKP KDTLMISRTP EVTCVVVDVS HEDPEVKFNW  300
YVDGVEVHNA KTKPREEQYN STYRVVSVLT VLHQDWLNGK EYKCKVSNKA LPAPIEKTIS  360
KAKGQPREPQ VYTLPPSRDE LTKNQVSLTC LVKGFYPSDI AVEWESNGQP ENNYKTTPPV  420
LDSDGSFFLY SKLTVDKSRW QQGNVFSCSV MHEALHNHYT QKSLSLSPGK             470

SEQ ID NO: 25          moltype = AA  length = 236
FEATURE                Location/Qualifiers
REGION                 1..236
                       note = light chain of hTKB1 with signal peptide
source                 1..236
                       mol_type = protein
                       organism = synthetic construct
SEQUENCE: 25
MDMRVPAQLL GLLLLWLRGA RCDIQMTQSP SSLSASVGDR VTITCKASQS VSNDVAWYQQ  60
KPGKAPKLLI YYASNRYTGV PSRFSGSGYG TDFTFTISSL QPEDIATYYC QQDYSSPLTF  120
GGGTKVEIKR TVAAPSVFIF PPSDEQLKSG TASVVCLLNN FYPREAKVQW KVDNALQSGN  180
```

-continued

```
SQESVTEQDS KDSTYSLSST LTLSKADYEK HKVYACEVTH QGLSSPVTKS FNRGEC      236

SEQ ID NO: 26          moltype = DNA  length = 1416
FEATURE                Location/Qualifiers
misc_feature           1..1416
                       note = coding region of heavy chain of hTKB1
source                 1..1416
                       mol_type = other DNA
                       organism = synthetic construct
SEQUENCE: 26
atgaaacacc tgtggttctt cctcctcctg gtggcagctc ccagatgggt cctgtcccaa  60
gttcagctgc aagaatccgg acccggactg gtgaagccct ccgagacttt atctttaact  120
tgtaccgtga gcggctactc catctcctcc ggctactact ggaactggat tcgtcagcct  180
cccggcaagg gtttagaatg gatgggctac atctcctacg acggctccaa caactacaac  240
ccctctttaa agaatcgtgt gaccatctct cgtgacacct ccaagaacca gttctcttta  300
aagctgtcct ccgtgacagc cgccgatacc gccgtgtact actgcgctcg tgcctactac  360
ggcaactacg tgggctactt cgacgtgtgg ggccaaggta ccaccgtgac agtctcctcc  420
gctagcacca agggcccatc ggtcttcccc ctggcaccct cctccaagag cacctctggg  480
ggcacagcgg ccctgggctg cctggtcaag gactacttcc ccgaaccggt gacggtgtcg  540
tggaactcag gcgccctgac cagcggcgtg cacaccttcc cggccgtcct acagtcctca  600
ggactctact ccctcagcag cgtggtgacc gtgccctcca gcagcttggg cacccagacc  660
tacatctgca acgtgaatca caagcccagc aacaccaagg tggacaagaa ggttgagccc  720
aaatcttgtg acaaaactca cacatgccca ccgtgcccag cacctgaagc agccggggga  780
ccgtcagtct tcctcttccc cccaaaaccc aaggacaccc tcatgatctc ccggacccct  840
gaggtcacat gcgtggtggt ggacgtgagc cacgaagacc ctgaggtcaa gttcaactgg  900
tacgtggacg gcgtggaggt gcataatgcc aagacaaagc cgcgggagga gcagtacaac  960
agcacgtacc gtgtggtcag cgtcctcacc gtcctgcacc aggactggct gaatggcaag  1020
gagtacaagt gcaaggtctc caacaaagcc ctcccagccc ccatcgagaa aaccatctcc  1080
aaagccaaag ggcagccccg agaaccacag gtgtacaccc tgcccccatc ccgggacgag  1140
ctgaccaaga accaggtcag cctgacctgc ctggtcaaag gcttctatcc cagcgacatc  1200
gccgtggagt gggagagcaa tgggcagccg gagaacaact acaagaccac gcctcccgtg  1260
ctggactccg acggctcctt cttcctctac agcaagctca ccgtggacaa gagcaggtgg  1320
cagcagggga acgtcttctc atgctccgtg atgcatgagg ctctgcacaa ccactacacg  1380
cagaagagcc tctccctgtc tccgggtaaa tgatga                            1416

SEQ ID NO: 27          moltype = DNA  length = 714
FEATURE                Location/Qualifiers
misc_feature           1..714
                       note = coding region of light chain of hTKB1
source                 1..714
                       mol_type = other DNA
                       organism = synthetic construct
SEQUENCE: 27
atggacatga gggtccccgc tcagctcctg gggctcctgc tactctggct ccgaggtgcc  60
agatgtgaca tccagatgac ccagtcccct tcctctttaa gcgcttccgt gggcgatcgt  120
gtgaccatca cttgtaaggc ctcccagtcc gtgtccaacg acgtggcttg gtaccagcag  180
aagcccggca aggcccccaa gctgctgatc tactacgcct ccaatcgtta caccggcgtg  240
ccttctcgtt tttccggctc cggctacggc accgacttca ccttcaccat ctcctcttta  300
cagcccgagg acatcgccac ctactactgc cagcaagatt actcctcccc tctgaccttt  360
ggcggcggca ccaaggtgga gatcaagcgt acggtggctg caccatctgt cttcatcttc  420
ccgccatctg atgagcagtt gaaatctgga actgcctctg ttgtgtgcct gctgaataac  480
ttctatccca gagaggccaa agtacagtgg aaggtggata acgccctcca atcgggtaac  540
tcccaggaga gtgtcacaga gcaggacagc aaggacagca cctacagcct cagcagcacc  600
ctgacgctga gcaaagcaga ctacgagaaa cacaaagtct acgcctgcga agtcacccat  660
cagggcctga gctcgcccgt cacaaagagc ttcaacaggg gagagtgttg atga        714

SEQ ID NO: 28          moltype = AA  length = 18
FEATURE                Location/Qualifiers
REGION                 1..18
                       note = signal peptide of heavy chain of hAKB1-A
source                 1..18
                       mol_type = protein
                       organism = synthetic construct
SEQUENCE: 28
MKVLSLLYLL TAIPGILS                                                18

SEQ ID NO: 29          moltype = AA  length = 18
FEATURE                Location/Qualifiers
REGION                 1..18
                       note = signal peptide of heavy chain of hAKB1-B
source                 1..18
                       mol_type = protein
                       organism = synthetic construct
SEQUENCE: 29
MKVLSLLYLL TAIPGILS                                                18

SEQ ID NO: 30          moltype = AA  length = 20
FEATURE                Location/Qualifiers
REGION                 1..20
```

-continued

```
                        note = signal peptide of light chain of hAKB1-A and hAKB1-B
source                  1..20
                        mol_type = protein
                        organism = synthetic construct
SEQUENCE: 30
MKSQTQVFVF LLLCVSGAHG                                              20

SEQ ID NO: 31           moltype = AA  length = 19
FEATURE                 Location/Qualifiers
REGION                  1..19
                        note = signal peptide of heavy chain of hTKB1
source                  1..19
                        mol_type = protein
                        organism = synthetic construct
SEQUENCE: 31
MKHLWFFLLL VAAPRWVLS                                               19

SEQ ID NO: 32           moltype = AA  length = 22
FEATURE                 Location/Qualifiers
REGION                  1..22
                        note = signal peptide of light chain of hTKB1
source                  1..22
                        mol_type = protein
                        organism = synthetic construct
SEQUENCE: 32
MDMRVPAQLL GLLLLWLRGA RC                                           22

SEQ ID NO: 33           moltype = DNA  length = 21
FEATURE                 Location/Qualifiers
misc_feature            1..21
                        note = Gapdh forward primer
source                  1..21
                        mol_type = other DNA
                        organism = synthetic construct
SEQUENCE: 33
cttcaccacc atggagaagg c                                            21

SEQ ID NO: 34           moltype = DNA  length = 21
FEATURE                 Location/Qualifiers
misc_feature            1..21
                        note = Gapdh reverse primer
source                  1..21
                        mol_type = other DNA
                        organism = synthetic construct
SEQUENCE: 34
ggcatggact gtggtcatga g                                            21

SEQ ID NO: 35           moltype = DNA  length = 22
FEATURE                 Location/Qualifiers
misc_feature            1..22
                        note = Ifng forward primer
source                  1..22
                        mol_type = other DNA
                        organism = synthetic construct
SEQUENCE: 35
accagagcat ccaaaagagt gt                                           22

SEQ ID NO: 36           moltype = DNA  length = 20
FEATURE                 Location/Qualifiers
misc_feature            1..20
                        note = Ifng reverse primer
source                  1..20
                        mol_type = other DNA
                        organism = synthetic construct
SEQUENCE: 36
ttagctgctg gcgacagttc                                              20

SEQ ID NO: 37           moltype = DNA  length = 21
FEATURE                 Location/Qualifiers
misc_feature            1..21
                        note = Tnfa forward primer
source                  1..21
                        mol_type = other DNA
                        organism = synthetic construct
SEQUENCE: 37
cagcctcttc tccttcctga t                                            21

SEQ ID NO: 38           moltype = DNA  length = 20
FEATURE                 Location/Qualifiers
```

-continued

```
misc_feature          1..20
                      note = Tnfa reverse primer
source                1..20
                      mol_type = other DNA
                      organism = synthetic construct
SEQUENCE: 38
gccagagggc tgattagaga                                             20

SEQ ID NO: 39         moltype = AA  length = 83
FEATURE               Location/Qualifiers
REGION                1..83
                      note = human Vk region for humanization
source                1..83
                      mol_type = protein
                      organism = synthetic construct
SEQUENCE: 39
DIQMTQSPSS LSASVGDRVT ITCWYQQKPG KAPKLLIYGV PSRFSGSGSG TDFTFTISSL  60
QPEDIATYYC FGGGTKVEIK RTV                                         83

SEQ ID NO: 40         moltype = AA  length = 87
FEATURE               Location/Qualifiers
REGION                1..87
                      note = VH region for humanization
source                1..87
                      mol_type = protein
                      organism = synthetic construct
SEQUENCE: 40
QVQLQESGPG LVKPSETLSL TCTVSGYSIS WIRQPPGKGL EWIGRVTISV DTSKNQFSLK  60
LSSVTAADTA VYYCARWGQG TTVTVSS                                     87
```

HUMANIZED ANTI-DNAM-1 ANTIBODY

CROSS-REFERENCE TO RELATED APPLICATIONS

This application is a continuation of U.S. patent application Ser. No. 18/717,538, filed Dec. 17, 2021, which is the United States national phase of International Patent Application No. PCT/JP2021/046786 filed Dec. 17, 2021, the disclosures of which are hereby incorporated by reference in their entirety.

REFERENCE TO A SEQUENCE LISTING

The Sequence Listing associated with this application is filed in electronic format via Patent Center and is hereby incorporated by reference into the specification in its entirety. The name of the file containing the Sequence Listing is 2407783.xml. The size of the file is 60, 877 bytes, and the file was created on Oct. 4, 2024.

BACKGROUND OF THE INVENTION

Field of the Invention

The present invention relates to a humanized anti-DNAM-1 antibody.

Description of Related Art

DNAM-1 is an adhesion molecule belonging to the immunoglobulin superfamily having a molecular weight of 65 kDa, also called CD226, and was identified as an activated immune receptor expressed in hematopoietic cells such as CD4+T cells, CD8+T cells, natural killer (NK) cells, and platelets.

When DNAM-1 binds to CD155 or CD112, which is a ligand thereof, DNAM-1 mediates an activation signal for cytotoxicity. DNAM-1 has been shown to be involved in various inflammatory diseases or cancer pathologies in human or mouse models. It has been reported that an anti-mouse DNAM-1 monoclonal antibody inhibits development of experimental autoimmune encephalitis and acute graft-versus-host disease (GVHD) in mice, increases a regulatory T (Treg) cell population, and as a result, prolongs a survival time of mouse skin grafts, for example. From these reports, the anti-DNAM-1 monoclonal antibody is considered to be useful in these diseases.

The present inventors have previously established a mouse anti-human DNAM-1 monoclonal antibody (Patent Literature 1: WO 2017/183665 A). In addition, a humanized anti-DNAM-1 antibody has also been reported (Non Patent Literature 1: Yumi Yamashita-Kanemaru et. al., Suppression of Th1 and Th17 Proinflammatory Cytokines and Upregulation of FOXP3 Expression by a Humanized Anti-DNAM-1 Monoclonal Antibody, MONOCLONAL ANTIBODIES IN IMMUNODIAGNOSIS AND IMMUNOTHERAPY, Volume 40, Number 2, 2021).

SUMMARY OF THE INVENTION

Technical Problem

Since the mouse anti-human DNAM-1 monoclonal antibody described in Patent Literature 1 activates regulatory T cells to inhibit an immune response, it is considered that the mouse anti-human DNAM-1 monoclonal antibody can be used for prevention or treatment of graft-versus-host disease, organ transplant rejection, autoimmune diseases, fibrotic diseases, inflammatory enteritis, and allergies, for example. However, the antibody established in Patent Literature 1 is only a mouse antibody, and there is room for improvement in terms of therapeutic value in humans, for example.

In addition, a humanized antibody generally has room for improvement in that a binding ability to a target antigen is reduced as compared with a parent mouse antibody, and immunogenicity tends to increase when the binding ability to the antigen is maintained, for example.

Therefore, the present inventors have considered to acquire a novel mouse anti-human DNAM-1 monoclonal antibody, and to produce a humanized anti-DNAM-1 antibody having a high therapeutic value in humans.

An object of the present invention is to provide a humanized anti-DNAM-1 antibody that specifically binds to human DNAM-1.

Solution to Problem

The present inventors have intensively studied to solve the above problems. As a result, the present inventors have found that the above problems can be solved by having the following configuration, thereby completing the present invention.

The present invention relates to, for example, the following [1] to [10].

[1] A humanized anti-DNAM-1 antibody or an antigen-binding fragment thereof, including:

a heavy chain variable region containing an amino acid sequence of SEQ ID NO: 1 as HCDR1, an amino acid sequence of SEQ ID NO: 2 as HCDR2, and an amino acid sequence of SEQ ID NO: 3 as HCDR3; and a light chain variable region containing an amino acid sequence of SEQ ID NO: 4 as LCDR1, an amino acid sequence of SEQ ID NO: 5 as LCDR2, and an amino acid sequence of SEQ ID NO: 6 as LCDR3.

[2] The humanized anti-DNAM-1 antibody or the antigen-binding fragment thereof according to [1], including a heavy chain variable region containing an amino acid sequence that is 95% or more identical to SEQ ID NO: 10 and a light chain variable region containing an amino acid sequence that is 95% or more identical to SEQ ID NO: 11.

[3] The humanized anti-DNAM-1 antibody or the antigen-binding fragment thereof according to [1] or [2], including:

a heavy chain variable region containing an amino acid sequence of SEQ ID NO: 10 and a light chain variable region containing an amino acid sequence of SEQ ID NO: 11; or a heavy chain variable region containing an amino acid sequence of SEQ ID NO: 9 and a light chain variable region containing an amino acid sequence of SEQ ID NO: 11.

[4] The humanized anti-DNAM-1 antibody or the antigen-binding fragment thereof according to any one of [1] to [3], in which the 238th and 239th amino acid residues of the heavy chain are A.

[5] The humanized anti-DNAM-1 antibody or the antigen-binding fragment thereof according to any one of [1] to [4], including a heavy chain containing an amino acid sequence that is 95% or more identical to SEQ ID NO: 14 and a light chain containing an amino acid sequence that is 95% or more identical to SEQ ID NO: 15.

[6] The humanized anti-DNAM-1 antibody according to any one of [1] to [5], including:

a heavy chain containing an amino acid sequence of SEQ ID NO: 14 and a light chain containing an amino acid sequence of SEQ ID NO: 15; or a heavy chain containing an amino acid sequence of SEQ ID NO: 13 and a light chain containing an amino acid sequence of SEQ ID NO: 15.

[7] A nucleic acid encoding the humanized anti-DNAM-1 antibody or the antigen-binding fragment thereof according to any one of [1] to [6].

[8] A vector containing the nucleic acid according to [7].

[9] A transformant containing the vector according to [8].

[10] An activation inhibitor for an innate lymphoid cell (ILC), containing the humanized anti-DNAM-1 antibody or the antigen-binding fragment thereof according to any one of [1] to [6].

Advantageous Effects of Invention

According to the present invention, a humanized anti-DNAM-1 antibody can be provided. In addition, an activation inhibitor for innate lymphoid cells (ILCs) can be provided.

BRIEF DESCRIPTION OF DRAWINGS

FIG. 1 illustrates a result of analyzing a binding ability of mAKB1 to human DNAM-1.

FIG. 2 illustrates amino acid sequences of heavy chain variable regions of mAKB1 (SEQ ID NO: 7) and a humanized antibody thereof (SEQ ID NOS: 9 hAKB1-VH1), 10 (hAKB1-VH2), and 40 (FJ039783 VH)). Back-mutated amino acid residues are shown in bold and CDRs are underlined.

FIG. 3 illustrates amino acid sequences of light chain variable regions of mAKB1 (SEQ ID NO: 8) and a humanized antibody thereof (SEQ ID NOS: 11 (hAKB1-VL1), 12 (hAKB1-VL2), and 39 (KU760971 VL)). Back-mutated amino acid residues are shown in bold and CDRs are underlined.

FIG. 4 illustrates a result of analyzing binding abilities of hAKB1-A, hAKB1-B, hAKB1-C, and hAKB1-D to human DNAM-1.

FIG. 5 illustrates a result of analyzing binding abilities of hAKB1-A and hAKB1-B to human DNAM-1.

FIG. 6 illustrates a base sequence of a heavy chain coding region of hAKB1-A.

FIG. 7 illustrates a base sequence of a heavy chain coding region of hAKB1-B.

FIG. 8 illustrates a base sequence of a light chain coding region of hAKB1-A and hAKB1-B.

FIG. 9 illustrates amino acid sequences of a heavy chain of hAKB1-A, a heavy chain of hAKB1-B, and a light chain of hAKB1-A and hAKB1-B.

FIG. 10 illustrates a base sequence of a heavy chain coding region of hTKB1.

FIG. 11 illustrates a base sequence of a light chain coding region of hTKB1.

FIG. 12 illustrates amino acid sequences of a heavy chain and a light chain of hTKB1.

FIG. 13A illustrates results of examining expression of DNAM-1 in innate lymphoid cells (ILCs) in the lung.

FIG. 13B illustrates results of examining expression of DNAM-1 in innate lymphoid cells (ILCs) in the intestine.

FIG. 14 illustrates results of analyzing expression levels of cytokines in ILCs using wild-type mice and DNAM-1 gene-deficient mice.

FIG. 15 is a diagram illustrating results of examining expression of DNAM-1 in innate lymphoid cells (ILCs) of human peripheral blood mononuclear cells (PBMCs).

FIG. 16 illustrates results of examining effects of mAKB1, hAKB1-A, hAKB1-B, and hTKB1 on cytokine production in innate lymphoid cells (ILCs).

DESCRIPTION OF THE INVENTION

Next, the present invention will be specifically described.

[Humanized Anti-DNAM-1 Antibody]

The term "humanized anti-DNAM-1 antibody" is used to mean a humanized antibody that specifically recognizes human DNAM-1. Specifically recognizing means that it binds to human DNAM-1 protein but does not bind to anything other than human DNAM-1 protein. The binding activity can be measured by a known method, for example, a method such as immunoprecipitation, Western blotting, enzyme immunoassay (EIA), enzyme-linked immunosorbent assay (ELISA), flow cytometry, or pull-down assay.

The humanized antibody is an antibody in which a variable region basically includes a complementary determining region (CDR) derived from a non-human antibody and a framework region (FR) derived from a human antibody, and a constant region includes a constant region derived from a human antibody.

A humanized anti-DNAM-1 antibody according to one aspect of the present invention includes:

a heavy chain variable region containing an amino acid sequence of SEQ ID NO: 1 as HCDR1, an amino acid sequence of SEQ ID NO: 2 as HCDR2, and an amino acid sequence of SEQ ID NO: 3 as HCDR3; and a light chain variable region containing an amino acid sequence of SEQ ID NO: 4 as LCDR1, an amino acid sequence of SEQ ID NO: 5 as LCDR2, and an amino acid sequence of SEQ ID NO: 6 as LCDR3. The humanized anti-DNAM-1 antibody refers to a humanized anti-DNAM-1 antibody (A).

The HCDR is a CDR of a heavy chain, and the LCDR is a CDR of a light chain.

The humanized anti-DNAM-1 antibody (A) may be an antibody that inhibits the binding between human DNAM-1 and a ligand thereof or an antibody that does not inhibit the binding between human DNAM-1 and a ligand thereof, and an antibody that inhibits the binding between human DNAM-1 and a ligand thereof is preferable. In addition, the humanized anti-DNAM-1 antibody (A) may be an antibody that inhibits or reduces signal transduction of human DNAM-1 (neutralizing antibody), an antibody that does not change signal transduction of human DNAM-1, or an antibody that promotes signal transduction of human DNAM-1 (agonistic antibody), and an antibody that inhibits or reduces signal transduction of human DNAM-1 (neutralizing antibody) is preferable.

A class and a subclass of the humanized anti-DNAM-1 antibody (A) are not particularly limited as long as the effect of the present invention is exerted, may be any of IgG, IgM, IgA, IgD, and IgE, and are preferably IgG, and more preferably IgG1. The heavy chain of the humanized anti-DNAM-1 antibody (A) may be any of γ, μ, α, δ, and ε, and is preferably γ, and more preferably γ1. The light chain of the humanized anti-DNAM-1 antibody (A) may be any of κ and λ, and is preferably κ.

As the humanized anti-DNAM-1 antibody (A), an antibody produced by a transformant or a culture supernatant of a transformant may be used as it is, or may be used after purification, for example. The purification can be performed, for example, by subjecting the humanized anti-DNAM-1 antibody (A) to affinity column chromatography such as saturated ammonium sulfate, ion exchange chromatography (DEAE or DE52, for example), an anti-immunoglobulin column, a protein A column, or a protein G column.

The humanized anti-DNAM-1 antibody (A) may be a multi-specific antibody, a recycling antibody, a sweeping antibody, or a conjugate antibody, for example. In addition, the humanized anti-DNAM-1 antibody may chemically or by gene engineering technique bind to functional molecules such as a non-peptide polymer such as polyethylene glycol (PEG), a radioactive substance, a toxin, a small molecule compound, a cytokine, a growth factor, albumin, an enzyme, and other antibodies. These antibodies can be produced by a known method.

A method for producing a humanized anti-DNAM-1 antibody (A) is not particularly limited, and the humanized anti-DNAM-1 antibody (A) can be produced by a known method. For example, the humanized anti-DNAM-1 antibody (A) can be obtained by transfecting a host cell with a vector containing a nucleic acid encoding a humanized anti-DNAM-1 antibody (A) to produce a transformant, and causing the transformant to produce a humanized anti-DNAM-1 antibody (A).

An amino acid sequence of the humanized anti-DNAM-1 antibody (A) is not particularly limited as long as it specifically recognizes human DNAM-1 in a region other than HCDR1 to HCDR3 and a region other than LCDR1 to LCDR3.

The humanized anti-DNAM-1 antibody (A) may preferably have a back mutation of an amino acid residue in a region other than HCDR1 to HCDR3 in the heavy chain variable region and/or in a region other than LCDR1 to LCDR3 in the light chain variable region.

The back mutation of the amino acid residue refers to a substitution of a single amino acid residue found in a human antibody framework for a corresponding amino acid residue found in a mouse antibody framework. Both low immunogenicity and a high binding ability to an antigen can be achieved by back mutation of an appropriate amino acid residue.

The number of back mutations of amino acid residues in the heavy chain variable region is preferably 1 to 6, and more preferably 1 to 3. The number of back mutations of amino acid residues in the light chain variable region is preferably 1 to 5, and more preferably 1 or 2.

The humanized anti-DNAM-1 antibody (A) may preferably have 1 to 3 back mutations of amino acid residues in a region other than HCDR1 to HCDR3 in the heavy chain variable region, and does not have a back mutation of an amino acid sequence in a region other than LCDR1 to LCDR3 in the light chain variable region.

The amino acid residue to be back-mutated can be selected within the variable region from amino acid residues that non-covalently bind directly to the antigen, amino acid residues adjacent to the CDR region, amino acid residues that interact with the CDR region, or amino acid residues that are involved in a VL-VH interface.

The back mutation of the amino acid residue in the heavy chain variable region is preferably carried out within a range of 5 amino acids before and after HCDR1, HCDR2, or HCDR3, and more preferably 2 amino acids.

The back mutation of the amino acid residue in the heavy chain variable region is preferably carried out at at least one amino acid residue selected from the 49th and 72nd amino acid residues in the heavy chain variable region. The back mutation of the amino acid residue in the light chain variable region is preferably carried out at the 67th amino acid residue in the light chain variable region.

The humanized anti-DNAM-1 antibody (A) more preferably has a back mutation at the 49th and 72nd amino acid residues in the heavy chain variable region and at the 67th amino acid residue in the light chain variable region.

Note that, in the present specification, the X-th amino acid residue means the X-th amino acid residue counting from the N-terminus of the protein without including the signal peptide.

In the back mutation of the amino acid residue in the heavy chain variable region, preferably, the 49th amino acid residue in the heavy chain variable region is set to M and the 72nd amino acid residue is set to R. In the back mutation of the amino acid residue in the light chain variable region, preferably, the 67th amino acid residue in the light chain variable region is set to Y.

The humanized anti-DNAM-1 antibody (A) more preferably has back mutations of I49M and V72R in the heavy chain variable region and a back mutation of S67Y in the light chain variable region.

The humanized anti-DNAM-1 antibody (A) preferably includes a heavy chain variable region containing an amino acid sequence that is 90% or more, 93% or more, 95% or more, 97% or more, 98% or more, or 99% or more identical to SEQ ID NO: 10, and a light chain variable region containing an amino acid sequence that is 90% or more, 93% or more, 95% or more, 97% or more, 98% or more, or 99% or more identical to SEQ ID NO: 11.

The percentage of sequence identity is determined by the sequence of the antibody maximally aligned according to Kabat numbering convention. After alignment, when comparing the target antibody region (for example, the light chain variable region) with the same region of a control antibody, the percentage of sequence identity between the target antibody region and the control antibody region is calculated by dividing the number of positions occupied by the same amino acid in both the target antibody region and the control antibody region by the total number of aligned positions in the two regions (gaps not counted) and multiplying by 100.

The humanized anti-DNAM-1 antibody (A) may be an antibody including a heavy chain variable region containing an amino acid sequence that is at least 95% or more identical to SEQ ID NO: 10 and has 1 to 6 mutations of amino acid residues in a region other than HCDR1 to HCDR3 in the amino acid sequence of SEQ ID NO: 10, and a light chain variable region containing an amino acid sequence that is at least 95% or more identical to SEQ ID NO: 11 and has 1 to 5 mutations of amino acid residues in a region other than LCDR1 to LCDR3 in the amino acid sequence of SEQ ID NO: 11. The mutation of the amino acid residue means substitution, insertion, or deletion of a single amino acid residue.

The humanized anti-DNAM-1 antibody (A) may be an antibody including a heavy chain variable region containing an amino acid sequence that is at least 97% or more identical to SEQ ID NO: 10 and has 1 to 3 mutations of amino acid residues in a region other than HCDR1 to HCDR3 in the amino acid sequence of SEQ ID NO: 10, and a light chain variable region containing an amino acid sequence that is at least 97% or more identical to SEQ ID NO: 11 and has 1 to 3 mutations of amino acid residues in a region other than LCDR1 to LCDR3 in the amino acid sequence of SEQ ID NO: 11.

Regarding the mutation of the amino acid residue, substitution is preferable among substitution, insertion, and deletion, and conservative substitution is more preferable. The "conservative substitution" is substitution of an amino acid residue with another chemically similar amino acid residue so as not to substantially alter the activity of the peptide. For example, examples thereof include a case in which a certain hydrophobic residue is substituted with another hydrophobic residue, and a case in which a certain polar residue is substituted with another polar residue having the same charge. Examples of chemically similar amino acids for which such substitution can be performed include alanine, valine, isoleucine, leucine, proline, tryptophan, phenylalanine, and methionine as non-polar (hydrophobic) amino acids. Examples of a polar (neutral) amino acid include glycine, serine, threonine, tyrosine, glutamine, asparagine, and cysteine. Examples of a positively charged (basic) amino acid include arginine, histidine, and lysine. In addition, examples of a negatively charged (acidic) amino acid include aspartic acid and glutamic acid.

The humanized anti-DNAM-1 antibody (A) preferably includes a heavy chain variable region containing an amino acid sequence that is 95% or more identical to SEQ ID NO: 10 and a light chain variable region containing an amino acid sequence that is 95% or more identical to SEQ ID NO: 11, in which the 49th and 72nd amino acid residues in the heavy chain variable region are M and R, respectively, and the 67th amino acid residue in the light chain variable region is Y.

The humanized anti-DNAM-1 antibody (A) preferably includes a heavy chain variable region containing an amino acid sequence of SEQ ID NO: 10 and a light chain variable region containing an amino acid sequence of SEQ ID NO: 11, or a heavy chain variable region containing an amino acid sequence of SEQ ID NO: 9 and a light chain variable region containing an amino acid sequence of SEQ ID NO: 11.

The humanized anti-DNAM-1 antibody (A) preferably contains a mutation of an amino acid residue that eliminates an effector function of an IgG antibody.

The mutation of the amino acid residue for eliminating the effector function of the IgG antibody is, for example, a mutation in which a branched chain amino acid such as valine (V), leucine (L), or isoleucine (I), a hydrophobic amino acid such as proline (P), methionine (M), or tryptophan (W), or an amino acid phosphorylated and involved in signal transduction, such as tyrosine (Y), serine(S), or threonine (T), is substituted with alanine (A) or phenylalanine (F) in the constant region of the heavy chain, and is preferably a mutation in which L is substituted with A or F, and more preferably a mutation in which two consecutive L are substituted with AA, FF, AF, or FA.

In the humanized anti-DNAM-1 antibody (A), the 238th and 239th amino acid residues of the heavy chain are preferably A or F, and more preferably both A. Such a humanized anti-DNAM-1 antibody (A) is useful for treatment of human diseases because it eliminates the effector function of the IgG antibody and hardly aggregates platelets.

The humanized anti-DNAM-1 antibody (A) preferably includes a heavy chain containing an amino acid sequence that is 90% or more, 93% or more, 95% or more, 97% or more, 98% or more, or 99% or more identical to SEQ ID NO: 14, and a light chain containing an amino acid sequence that is 90% or more, 93% or more, 95% or more, 97% or more, 98% or more, or 99% or more identical to SEQ ID NO: 15.

The humanized anti-DNAM-1 antibody (A) is preferably an antibody including a heavy chain variable region containing an amino acid sequence that is at least 95% or more identical to SEQ ID NO: 14 and has 1 to 22 mutations of amino acid residues in a region other than HCDR1 to HCDR3 in the amino acid sequence of SEQ ID NO: 14, and a light chain variable region containing an amino acid sequence that is at least 95% or more identical to SEQ ID NO: 15 and has 1 to 10 mutations of amino acid residues in a region other than LCDR1 to LCDR3 in the amino acid sequence of SEQ ID NO: 15.

The humanized anti-DNAM-1 antibody (A) is preferably an antibody including a heavy chain variable region containing an amino acid sequence that is at least 97% or more identical to SEQ ID NO: 14 and has 1 to 13 mutations of amino acid residues in a region other than HCDR1 to HCDR3 in the amino acid sequence of SEQ ID NO: 14, and a light chain variable region containing an amino acid sequence that is at least 97% or more identical to SEQ ID NO: 15 and has 1 to 6 mutations of amino acid residues in a region other than LCDR1 to LCDR3 in the amino acid sequence of SEQ ID NO: 15.

The humanized anti-DNAM-1 antibody (A) preferably includes a heavy chain containing an amino acid sequence that is 95% or more identical to SEQ ID NO: 14 and a light chain containing an amino acid sequence that is 95% or more identical to SEQ ID NO: 15, in which the 49th and 72nd amino acid residues in the heavy chain variable region are M and R, respectively, and the 67th amino acid residue in the light chain variable region is Y.

The humanized anti-DNAM-1 antibody (A) includes a heavy chain containing an amino acid sequence of SEQ ID NO: 14 and a light chain containing an amino acid sequence of SEQ ID NO: 15, or a heavy chain containing an amino acid sequence of SEQ ID NO: 13 and a light chain containing an amino acid sequence of SEQ ID NO: 15.

[Antigen-Binding Fragment of Humanized Anti-DNAM-1 Antibody]

An antigen-binding fragment of the humanized anti-DNAM-1 antibody is a protein containing a part of the humanized anti-DNAM-1 antibody (A), and refers to a protein capable of binding to an antigen. Examples of the antigen-binding fragment include F(ab')2, Fab', Fab, disulfide bond stabilized Fv (dsFv), a single chain antibody (scFv), a diabody, and a polymer thereof.

Fab is an antibody fragment having an antigen-binding activity and a molecular weight of about 50,000 among fragments obtained by treating IgG with papain (protease). Fab of the humanized anti-DNAM-1 antibody can be prepared by treating the humanized anti-DNAM-1 antibody with papain, or inserting DNA encoding the Fab of the antibody into an expression vector, introducing the vector into prokaryotes or eukaryotes, and expressing the vector.

F(ab')2 is an antibody fragment having an antigen-binding activity and a molecular weight of about 100,000 among fragments obtained by treating IgG with pepsin (protease). F(ab')2 of the humanized anti-DNAM-1 antibody can be prepared by treating the humanized anti-DNAM-1 antibody with pepsin or bonding Fab' (described below) with a thioether bond or a disulfide bond.

Fab' is an antibody fragment having an antigen-binding activity and a molecular weight of about 50,000 in which a disulfide bond in a hinge region of F(ab')2 is cleaved. Fab' of the humanized anti-DNAM-1 antibody can be prepared by treating F(ab')2 of the humanized anti-DNAM-1 antibody with dithiothreitol, or inserting DNA encoding the Fab' of the antibody into an expression vector, introducing the vector into prokaryotes or eukaryotes, and expressing the vector.

scFv is an antibody fragment having an antigen-binding activity in which one VH and one VL are linked using an appropriate peptide linker. scFv of the humanized anti-DNAM-1 antibody can be prepared by obtaining cDNA encoding VH and VL of the humanized anti-DNAM-1 antibody, constructing DNA encoding scFv, inserting the DNA into an expression vector, introducing the expression vector into prokaryotes or eukaryotes, and expressing the vector.

A diabody is an antibody fragment in which scFv is dimerized, and is an antibody fragment having a divalent antigen-binding activity. A diabody of the humanized anti-DNAM-1 antibody can be prepared by obtaining cDNA encoding VH and VL of the humanized anti-DNAM-1 antibody, constructing DNA encoding a diabody, inserting the DNA into an expression vector, introducing the expression vector into prokaryotes or eukaryotes, and expressing the vector.

dsFv is an antibody fragment in which a polypeptide obtained by substituting one amino acid residue in each of VH and VL with a cysteine residue is bonded via a disulfide bond between cysteine residues. dsFv of the humanized anti-DNAM-1 antibody can be prepared by obtaining cDNA encoding VH and VL of the humanized anti-DNAM-1 antibody, constructing DNA encoding dsFv, inserting the DNA into an expression vector, introducing the expression vector into prokaryotes or eukaryotes, and expressing the vector.

The antigen-binding fragment may chemically or genetically bind to functional molecules such as a non-peptide polymer such as polyethylene glycol (PEG), a radioactive substance, a toxin, a small molecule compound, a cytokine, a growth factor, albumin, an enzyme, and other antibodies.

The antigen-binding fragments may be used alone or in combination of two or more kinds thereof. In addition, the humanized anti-DNAM-1 antibody and the antigen-binding fragment thereof may be used in combination.

[Nucleic Acid Encoding Humanized Anti-DNAM-1 Antibody or Antigen-Binding Fragment Thereof]

One aspect of the present invention is a nucleic acid encoding the humanized anti-DNAM-1 antibody (A) or the antigen-binding fragment thereof.

Examples of the nucleic acid include a nucleic acid encoding the heavy chain variable region of the humanized anti-DNAM-1 antibody (A), a nucleic acid encoding the light chain variable region of the humanized anti-DNAM-1 antibody (A), a nucleic acid encoding a part of the heavy chain variable region and the constant region of the humanized anti-DNAM-1 antibody (A), a nucleic acid encoding a part of the light chain variable region and the constant region of the humanized anti-DNAM-1 antibody (A), a nucleic acid encoding the entire length of the heavy chain of the humanized anti-DNAM-1 antibody (A), a nucleic acid encoding the entire length of the light chain of the humanized anti-DNAM-1 antibody (A), and a nucleic acid encoding scFv in which the heavy chain variable region and the light chain variable region of the humanized anti-DNAM-1 antibody (A) are linked by an appropriate linker.

The nucleic acid can be produced using a known genetic engineering technique.

It is preferable to add a nucleic acid encoding a signal peptide to a nucleic acid encoding the humanized anti-DNAM-1 antibody (A) or the antigen-binding fragment thereof. When a signal peptide of an appropriate amino acid sequence is added, an expression level of the humanized anti-DNAM-1 antibody (A) or the antigen-binding fragment thereof in cells or the amount of the antibody or the antigen-binding fragment secreted to a culture supernatant can be increased.

The amino acid sequence of the signal peptide is not particularly limited, and in the heavy chain, the amino acid sequence is preferably an amino acid sequence set forth in SEQ ID NO: 28, SEQ ID NO: 29, or SEQ ID NO: 31, and more preferably an amino acid sequence set forth in SEQ ID NO: 31. The amino acid sequence of the signal peptide is, in the light chain, preferably an amino acid sequence set forth in SEQ ID NO: 30 or SEQ ID NO: 32, and more preferably an amino acid sequence set forth in SEQ ID NO: 32.

The nucleic acid encoding the full length of the heavy chain to which the signal peptide is added is preferably a nucleic acid encoding an amino acid sequence set forth in SEQ ID NO: 16, SEQ ID NO: 17, or SEQ ID NO: 24, more preferably a nucleic acid encoding an amino acid sequence set forth in SEQ ID NO: 24, still more preferably a nucleic acid consisting of a base sequence set forth in SEQ ID NO: 19 or SEQ ID NO: 20, or SEQ ID NO: 26, and particularly preferably a nucleic acid consisting of a base sequence set forth in SEQ ID NO: 26.

The nucleic acid encoding the full length of the light chain to which the signal peptide is added is preferably a nucleic acid encoding an amino acid sequence set forth in SEQ ID NO: 18 or SEQ ID NO: 25, more preferably a nucleic acid encoding an amino acid sequence set forth in SEQ ID NO: 25, still more preferably a nucleic acid consisting of a base sequence set forth in SEQ ID NO: 21 or SEQ ID NO: 27, and particularly preferably a nucleic acid consisting of a base sequence set forth in SEQ ID NO: 27.

[Vector Containing Nucleic Acid]

One aspect of the present invention is a vector containing a nucleic acid encoding the humanized anti-DNAM-1 antibody (A) or the antigen-binding fragment thereof. In other words, one aspect of the present invention is a recombinant vector incorporating a nucleic acid encoding the humanized anti-DNAM-1 antibody (A) or the antigen-binding fragment thereof.

The vector is not particularly limited, and examples thereof include a plasmid vector and a viral vector. The vector may be a vector that can be expressed in, for example, mammals, bacteria, insects, yeast, and fungi, a vector that can be expressed in eukaryotic cells is preferable, and a vector that can be expressed in cells derived from mammals is more preferable. Examples of the vector that can be expressed in cells derived from mammals include pUC series, pCAG, pEBMulti, pEGFP-C1, pEGFP-C1, pEF-BOS, pTRE-Myc, pMSCVpuro, and pCEP4, and pUC19 is preferable.

A method for producing a vector is not particular limited, and the vector can be produced by a known genetic recombination technique.

In addition to the nucleic acid encoding the humanized anti-DNAM-1 antibody (A) or the antigen-binding fragment thereof, the vector may contain a regulatory control sequence capable of controlling replication and expression in a host and/or secretion from the host. Examples of the regulatory control sequence include a promoter sequence such as a CMV promoter.

[Transformant Containing Vector]

One aspect of the present invention is a transformant containing a vector containing a nucleic acid encoding the humanized anti-DNAM-1 antibody (A) or the antigen-binding fragment thereof. The humanized anti-DNAM-1 antibody (A) or the antigen-binding fragment thereof can be obtained from a transformant, or a culture supernatant thereof, for example.

The transformant can be obtained by introducing the above-described recombinant vector into a host. Examples of the host include cultured cells such as *E. coli*, yeast, plant cells, insect cells, and animal cells, insect organisms such as silkworms, and plants such as tobacco, and animal cells are preferable.

Examples of the animal cells include mammalian cells such as NSO, Sp2/0, CHO, COS, HEK, fibroblasts, and myeloma cells, and CHO is preferable.

The introduction (transformation) of the recombinant vector into the host can be performed using a known method. Examples of such a method include a competent cell method using a cell body treated with calcium and an electroporation method. In addition, a method of infecting a host with a phage vector or a viral vector, for example, in addition to a plasmid vector, to transform the host may be used.

[Activation Inhibitor for Innate Lymphoid Cell (ILC)]

One aspect of the present invention is an activation inhibitor for an innate lymphoid cell (ILC) containing the humanized anti-DNAM-1 antibody (A) or the antigen-binding fragment thereof.

One aspect of the present invention is a humanized anti-DNAM-1 antibody (A) or an antigen-binding fragment thereof for use in activation inhibition of an innate lymphoid cell (ILC).

One aspect of the present invention is a method for inhibiting activation of an innate lymphoid cell (ILC), the method including administering an effective amount of the humanized anti-DNAM-1 antibody (A) or the antigen-binding fragment thereof to a subject.

The innate lymphoid cells (ILCs) are cells of innate immune system derived from lymphoid progenitor cells (CLPs). Since the ILC has neither a T cell receptor nor a B cell receptor, it is known that the ILC is not activated in an antigen-specific manner, but is rapidly activated by antigen-independent stimulation to produce a large amount of cytokines.

The ILC can be classified into three subsets of ILC1 that differentiates in a T-bet-dependent manner and produces IFN-γ; ILC2 differentiates in a GATA-3-dependent manner and produces IL-5, IL-9, and IL-13; and ILC3 that expresses RORγt and produces IL-22 or IL-17.

The ILC is a tissue-resident cell, and interacts with not only immune cells but also non-immune cells to contribute to maintenance of tissue homeostasis. From the properties of the ILC to localize in tissue and produce a large amount of cytokines in response to non-antigen-specific stimulation, it is considered that its inappropriate activation leads to pathological formation. However, much remains to be learned about for example, a mechanism of activation, such as a molecule through which an ILC is activated.

It is considered that the ILC is associated with lung diseases such as asthma, chronic obstructive pulmonary disease (COPD), and pulmonary fibrosis; inflammatory bowel diseases such as ulcerative colitis and Crohn's disease; autoimmune diseases such as multiple sclerosis, rheumatoid arthritis, and psoriasis; infectious diseases such as viral infections, bacterial infections, parasitic infections, and protozoal infections; and acute and chronic liver disorders, for example.

The activation of the ILC can be indicated by an increase in the number of cells of ILC, and an increase in cytokines such as IFN-γ, IL-5, IL-9, IL-13, IL-22, IL-17, GM-CSF, and TNF-α produced by ILCs, for example.

The activation inhibitor for ILCs may decrease any of the above indices related to the activation of ILCs. The activation inhibitor for ILCs is preferably a cytokine production inhibitor, and more preferably an IFN-γ production inhibitor or a TNF-α production inhibitor.

As described below in Examples, the humanized anti-DNAM-1 antibody (A) or the antigen-binding fragment thereof can inhibit activation of innate lymphoid cells, particularly cytokine production.

Therefore, it is presumed that the humanized anti-DNAM-1 antibody (A) or the antigen-binding fragment thereof exhibits the effect in prevention and treatment of diseases related to activation of innate lymphoid cells, for example, lung diseases such as asthma, chronic obstructive pulmonary disease (COPD), and pulmonary fibrosis; inflammatory bowel diseases such as ulcerative colitis and Crohn's disease; autoimmune diseases such as multiple sclerosis, rheumatoid arthritis, and psoriasis; infectious diseases such as viral infections, bacterial infections, parasitic infections, and protozoal infections; and acute and chronic liver disorders.

WO 2017/183665 A describes that the anti-DNAM-1 antibody can be used to prevent or treat graft-versus-host disease, organ transplant rejection, autoimmune diseases, fibrotic diseases, inflammatory enteritis, and allergies, for example, because it activates regulatory T cells and inhibits immune responses. The present inventors have found that DNAM-1 is expressed in ILCs of lung, intestine, and PBMCs as described below in Examples. Furthermore, it was found that DNAM-1 is involved in the activation of ILCs, particularly cytokine production, and that the humanized anti-DNAM-1 antibody can inhibit the activation of ILCs. Among the diseases for which the anti-DNAM-1 antibody can be used to prevent or treat, in particular, in patients with lung diseases such as asthma, chronic obstructive pulmonary disease (COPD), and pulmonary fibrosis; inflammatory bowel diseases such as ulcerative colitis and Crohn's disease; autoimmune diseases such as multiple sclerosis, rheumatoid arthritis, and psoriasis; infectious diseases such as viral infections, bacterial infections, parasitic infections, and protozoal infections; and acute and chronic liver disorders, it is considered that some patients have activated ILCs and others do not. The novel findings described in the present specification allow selective administration of the humanized anti-DNAM-1 antibody (A) to patients with ILC activation, which is expected to increase the therapeutic outcome. In addition, the dose, the timing of administration, and the schedule of the humanized anti-DNAM-1 antibody (A) can be determined using the activation of ILCs as an index.

EXAMPLES

Next, the present invention will be described in more detail with reference to Examples, but the present invention is not limited thereto.

All experiments were performed in accordance with the guidelines of the Animal Ethics Committee of the Center for Experimental Animal Resources, University of Tsukuba.

[Experimental Example 1] Preparation of Anti-Human DNAM-1 Humanized Antibody

[Preparation of Anti-Human DNAM-1 Monoclonal Antibody (mAKB1)]

Human DMAM-1 gene was introduced into a BW5147 cell line, which is a mouse lymphocyte cell, to express human DMAM-1 protein. A mouse was immunized with the cells as an antigen, and spleen cells were collected from the mouse and fused with SP2/0 myeloma cells by a conventional method to obtain hybridomas. The hybridomas were screened using reactivity to human DNAM-1 protein as an index, and the selected clone was defined as clone mAKB1. An antibody produced by mAKB1 is referred to as anti-human DNAM-1 monoclonal antibody mAKB1 (also simply referred to as mAKB1). A binding ability to human DNAM-1 was analyzed using mAKB1 obtained by purifying a culture supernatant of clone mAKB1 with a protein A sepharose column.

[Analysis of Binding Ability to Human DNAM-1]

Binding to human DNAM-1 was examined by flow cytometry using a mouse lymphoblast BW5147 cell line (hereinafter, may be referred to as "BW") and BW5147 stably expressing human hDNAM-1 (hereinafter, may be referred to as "hDNAM-1/BW"). Test antibodies at various concentrations were incubated with about 105 hDNAM-1/BW cells at 4° C. for 1 hour in PBS (FACS buffer) containing 0.5% BSA and 0.05% NaN3. Thereafter, the cells were washed with ice-cooled FACS Buffer, and incubated at 4° C. for 30 minutes using a PE-labeled goat anti-human IgG antibody (manufactured by SouthernBiotech). After washing with FACS buffer, the stained cells were analyzed using a FACScan flow cytometer (manufactured by BD Biosciences).

FIG. 1 illustrates a result of analyzing a binding ability of mAKB1 to human DNAM-1. mAKB1 was specifically bound to human DNAM-1, and $EC_{50}$ was 6 μg/mL.

[Sequencing of mAKB1]

The genes of the heavy chain variable region and the light chain variable region of the anti-human DNAM-1 monoclonal antibody mAKB1 were cloned from the clone mAKB1 by a conventional method, and the base sequences of the heavy chain variable region and the light chain variable region of mAKB1 were identified. The amino acid sequence was deduced from the base sequence, and CDRs were determined by the method of Kabat using abYsis.

[Design of VH and VL Genes of Humanized Antibody hAKB1]

Based on mAKB1, the amino acid sequences of VH (heavy chain variable region) and VL (light chain variable region) of the humanized antibody were designed as follows. First, a three-dimensional molecular model of the mAKB1 variable region was constructed. Using the molecular model, framework amino acid residues important for the formation of the three-dimensional structure of CDRs were identified.

Human VH sequences homologous to the mAKB1 VH framework were retrieved in the GenBank database and a VH sequence encoded by human FJ039783 CDNA (FJ039783 VH) was selected as an acceptor for humanization.

The HCDR sequence of mAKB1 was grafted to the corresponding position of FJ039783 VH. The 30th, 49th and 72nd amino acid residues in the heavy chain variable region were substituted from the amino acid residue of FJ039783 VH to the corresponding residue of mAKB1 VH since they were considered important for the formation of the CDR structure. VH of the obtained humanized antibody was defined as hAKB1-VH1. Furthermore, in order to reduce immunogenicity, hAKB1-VH2 in which the 30th amino acid residue was not back-mutated to an amino acid residue of a mouse was additionally designed. The amino acid sequences of VH of mAKB1 (SEQ ID NO: 7), hAKB1-VH1 (SEQ ID NO: 9), hAKB1-VH2 (SEQ ID NO: 10), and FJ039783 VH (SEQ ID NO: 40) are illustrated in FIG. 2.

Human VL sequences homologous to the mAKB1 VL framework were retrieved in the GenBank database and a human VK region encoded by KU760971 CDNA (KU760971 VL) was selected as an acceptor for humanization.

The LCDR sequence of mAKB1 was grafted to the corresponding position of KU760971 VL. The 67th amino acid residue in the light chain variable region was substituted from the amino acid residue of KU760971 VL to the corresponding residue of mAKB1 VL since it was considered important for the formation of the CDR structure. VL of the obtained humanized antibody was defined as hAKB1-VL1. Furthermore, in order to reduce immunogenicity, hAKB1-VL2 in which the 67th amino acid residue was not back-mutated to an amino acid residue of a mouse was additionally designed. The amino acid sequences of VL of mAKB1 (SEQ ID NO: 8), hAKB1-VL1 (SEQ ID NO: 11), hAKB1-VL2 (SEQ ID NO: 12), and KU760971 VL (SEQ ID NO: 39) are illustrated in FIG. 3.

[Construction of VH and VL Genes of Humanized Antibodies]

Genes encoding hAKB1-VH1, hAKB1-VH2, hAKB1-VL1, and hAKB1-VL2 were synthesized including a signal peptide, a splice donor signal, and restriction enzyme sites at the 5' and 3' ends. The synthesized genes were incorporated into plasmids in the following combination to produce expression vectors.

TABLE 1

| Expression vector name | Heavy chain | Light chain |
|---|---|---|
| phAKB1-A | hAKB1-VH1 | hAKB1-VL1 |
| phAKB1-B | hAKB1-VH2 | hAKB1-VL1 |
| phAKB1-C | hAKB1-VH1 | hAKB1-VL2 |
| phAKB1-D | hAKB1-VH2 | hAKB1-VL2 |

Using polyethyleneimine, each of four expression vectors (phAKB1-A, phAKB1-B, phAKB1-C, and phAKB1-D4) was transfected into the human embryonic kidney cell line HEK293. HEK293 cells were cultured in a 7.5% $CO_2$ incubator at 37° C. using DMEM medium containing 10% FBS (manufactured by Hyclone Laboratories Inc.). Expression of antibodies in the culture supernatant of transiently transfected HEK293 cells was confirmed by ELISA. An ELISA plate was coated with goat anti-human IgG diluted to 1/2,000 with PBS and Fcγ-specific polyclonal antibody (manufactured by Sigma-Aldrich) at 100 μl/well and 4° C. overnight, and the plate was washed with a washing buffer (PBS containing 0.05% Tween20) and blocked with an ELISA buffer (PBS containing 2% skim milk and 0.05% Tween20) at 300 μl/well. After washing with a washing buffer, 100 μl/well of the test antibody appropriately diluted with an ELISA buffer was applied to the ELISA plate. A humanized IgG1/kappa antibody was used as a standard. The ELISA plate was incubated at room temperature for 1 hour and washed with a washing buffer, and then a bound antibody was detected using 100 μl/well of HRP-conjugated goat anti-human kappa chain polyclonal antibodies (manufactured by Bethyl Laboratories) diluted to 1/2,000. The ELISA plate was incubated at room temperature for 0.5 hours and washed with a washing buffer, 100 μl/well of ABTS substrate (manufactured by Sigma-Aldrich) was added to start color development, and the incubation was stopped with 100 μl/well of 2% oxalic acid. Absorbance at 405 nm was read.

[Binding Ability of Humanized Antibody to Antigen]

Antibodies produced by cells transfected with phAKB1-A, phAKB1-B, phAKB1-C, or phAKB1-D were defined as hAKB1-A, hAKB1-B, hAKB1-C, and hAKB1-D, respectively. Binding abilities of these antibodies to human DNAM-1 were analyzed as described above in "Analysis of binding ability to human DNAM-1". The results are illustrated in FIG. 4.

The binding abilities of hAKB1-A and hAKB1-B to human DNAM-1 were higher than those of hAKB1-C and hAKB1-D. In the antibody containing hAKB1-VL1 (hAKB1-A or hAKB1-B) and the antibody containing hAKB1-VL2 (hAKB1-C or hAKB1-D), a difference in binding ability to the antigen was observed, and the 67th amino acid residue of hAKB1-VL1 was changed from Tyr to Ser, such that the binding ability was reduced. There was no difference in binding ability to the antigen between hAKB1-A and hAKB1-B.

[Establishment of Cell Line Stably Producing Antibody]

In order to obtain a cell line stably producing hAKB1-A or hAKB1-B having a high binding ability to human DNAM-1, the expression vectors phAKB1-A and phAKB1-B each were introduced into the chromosome of Chinese hamster ovary cell line CHO-K1 (obtained from ATCC) by the following method.

CHO-K1 cells were cultured in a 7.5% $CO_2$ incubator at 37° C. using SFM4CHO medium (manufactured by Hyclone Laboratories Inc.). Transfection into CHO-K1 was performed by electroporation. Prior to the transfection, each expression vector was linearized using FspI. About $2.5\times10^6$ cells were transfected with 20 μg of a linearized plasmid and suspended in SFM4CHO medium, the cells were appropriately diluted, and then the cells were plated in a plurality of 96-well plates. After 48 hours, 10 μg/ml of puromycin was added and stable transfectants were separated. About 10 days after the start of the selection, antibody production of the culture supernatant of the transfectant placed in the 96-well plate was measured by sandwich ELISA by the method described above. CHO-K1 stable transfectants producing hAKB1-A or hAKB1-B at high levels were selected and subjected to the next culture.

CHO-K1 stable transfectants were cultured with 450 ml of SFM4CHO in a roller bottle so as to have a density of about $3\times10^6$ cells/ml, 50 ml of 35 mg/ml Cell Boost 4 (manufactured by Hyclone Laboratories Inc.) was added, and culture was further performed until a cell viability reached 50% or less. After centrifugation and filtration, the culture supernatant was loaded onto Protein A Sepharose column (HiTrap MabSelect SuRe, manufactured by GE Healthcare Technologies, Inc.). After washing the column with PBS, antibodies were eluted with a 0.1 M glycine-HCl buffer (pH 3.0) containing 0.1 M NaCl. After neutralization with 1 M Tris-HCl (pH 8.0), the buffer of eluted antibodies was exchanged into PBS by dialysis.

Characteristics of the purified hAKB1-A and hAKB1-B were investigated by SDS-PAGE according to a standard procedure. As a result of analysis under reducing conditions, it was found that each of these antibodies was composed of a heavy chain having a molecular weight of about 50 kDa and a light chain having a molecular weight of about 25 kDa. In addition, it was found that the purity of each antibody was 95% or more.

For the purified hAKB1-A and hAKB1-B, ECs with human DNAM-1 was determined by the method of "Analysis of binding ability to human DNAM-1" described above. The results are illustrated in FIG. 5.

$EC_{50}$ of hAKB1-A and hAKB1-B were 5 μg/mL and 5 μg/mL, respectively, and the binding ability to human DNAM-1 was equivalent or higher than that of mAKB1 in which humanization was based.

RNA was extracted from CHO-K1/hAKB1-A and CHO-K1/hAKB1-B, and PCR was performed to confirm the base sequences of the heavy chain and light chain of hAKB1-A and hAKB1-B produced by CHO-K1/hAKB1-A and CHO-K1/hAKB1-B.

The base sequences of the coding regions of the obtained heavy chains and light chains of hAKB1-A and hAKB1-B were completely matched with the corresponding base sequences of the phAKB1-A and phAKB1-B vectors. The base sequences (SEQ ID NO: 19, SEQ ID NO: 20, and SEQ ID NO: 21) of the coding regions of the heavy chains and the light chains of hAKB1-A and hAKB1-B are illustrated in FIGS. 6 to 8, respectively. In addition, the amino acid sequence was deduced from the base sequence, the variable region was further determined, and CDRs were determined by the method of Kabat using abYsis. The results are illustrated in FIG. 9. The signal peptide is indicated by a white character, the variable region is indicated by a bold, and the CDR is indicated by an underline.

The amino acid sequence (with a signal peptide) of the heavy chain of hAKB1-A of SEQ ID NO: 16 is composed of the amino acid sequence (SEQ ID NO: 28) of the signal peptide of the heavy chain of hAKB1-A and the amino acid sequence (without a signal peptide: SEQ ID NO: 13) of the heavy chain of hAKB1-A.

The amino acid sequence (with a signal peptide) of the heavy chain of hAKB1-B of SEQ ID NO: 17 is composed of the amino acid sequence (SEQ ID NO: 29) of the signal peptide of the heavy chain of hAKB1-B and the amino acid sequence (without a signal peptide: SEQ ID NO: 14) of the heavy chain of hAKB1-B.

The amino acid sequence (with a signal peptide) of the light chain of hAKB1-A and hAKB1-B of SEQ ID NO: 18 is composed of the amino acid sequence (SEQ ID NO: 30) of the signal peptide of the light chain of hAKB1-A and hAKB1-B and the amino acid sequence (without a signal peptide: SEQ ID NO: 15) of the light chain of hAKB1-A and hAKB1-B.

The amino acid sequences of HCDR1, HCDR2, HCDR3, LCDR1, LCDR2, and LCDR3 of hAKB1-A and hAKB1-B were common, and were SEQ ID NO: 1, SEQ ID NO: 2, SEQ ID NO: 3, SEQ ID NO: 4, SEQ ID NO: 5, and SEQ ID NO: 6, respectively.

[Establishment of hTKB1]

In order to establish a cell line that is permanently stable, efficiently produces hAKB1-B, and sufficiently secretes hAKB1-B extracellularly, the signal peptide sequences of the heavy chain and the light chain of hAKB1-B were modified.

A nucleic acid fragment consisting of a sequence in which a base sequence encoding a modified signal peptide was bound to the upstream of the base sequence of the coding region of the heavy chain and the light chain of hAKB1-B was incorporated into each of expression vectors pwX068 and pwX069 in tandem. The nucleic acid fragment was introduced into competent *E. coli* TOP10 (CB104-2, manufactured by TIANGEN Biotech (Beijing) Co., Ltd.), and an expression vector incorporating an antibody gene was amplified and recovered. The nucleic acid fragment was linearized with FspI (R0135L, manufactured by NEB, Inc.) and then introduced into the chromosome of CHO-K1. According to the method described above in "Establishment of cell line stably producing antibody", a CHO-K1 stable transfectant into which an expression vector of pWX069 that produces hAKB1-B at a high level and secretes pWX069 with high efficiency was introduced was selected. The obtained cell line was defined as CHO-K1/hTKB1, and the antibody produced by this cell line was defined as hTKB1.

The base sequences (SEQ ID NO: 26 and SEQ ID NO: 27) of the coding regions of the heavy chain and the light chain of hTKB1 are illustrated in FIGS. 10 and 11, respectively. The signal peptide is indicated by a white character, and the variable region is indicated by a bold.

In addition, the amino acid sequence was deduced from the base sequence, the variable region was further determined, and CDRs were determined by the method of Kabat using abYsis. The results are illustrated in FIG. 12. The signal peptide is indicated by a white character, the variable region is indicated by a bold, and the CDR is indicated by an underline.

The amino acid sequences of the heavy chain and the light chain of hTKB1 were the same as the amino acid sequences of the heavy chain and the light chain of hAKB1-B, respectively, except for the signal peptide. That is, the amino acid sequence of SEQ ID NO: 22 is the same as the amino acid sequence of SEQ ID NO: 14, and the amino acid sequence of SEQ ID NO: 23 is the same as the amino acid sequence of SEQ ID NO: 15.

The amino acid sequences of HCDR1, HCDR2, HCDR3, LCDR1, LCDR2, and LCDR3 of hTKB1 were the same as the amino acid sequences of HCDR1, HCDR2, HCDR3, LCDR1, LCDR2, and LCDR3 of hAKB1-A and hAKB1-B, respectively.

The amino acid sequence (with a signal peptide) of the heavy chain of hTKB1 of SEQ ID NO: 24 is composed of the amino acid sequence (SEQ ID NO: 31) of the signal peptide of the heavy chain of hTKB1 and the amino acid sequence (without a signal peptide: SEQ ID NO: 22) of the heavy chain of hTKB1.

The amino acid sequence (with a signal peptide) of the light chain of hTKB1 of SEQ ID NO: 25 is composed of the amino acid sequence (SEQ ID NO: 32) of the signal peptide of the light chain of hTKB1 and the amino acid sequence (without a signal peptide: SEQ ID NO: 23) of the light chain of hTKB1.

[Expression Analysis of DNAM-1 in ILCs]

(Method)

Lungs of mice (C57BL/6J, 8 to 10 weeks old, female) were perfused with PBS, isolated, treated with collagenase IV (5 mg/ml, manufactured by Sigma-Aldrich) at 37° C. for 1 hour, and then homogenized using gentleMACS Dissociator (manufactured by Miltenyi Biotec).

The large intestines of the mice were dissected, incised, washed twice with phosphate buffered saline (PBS) containing 0.5% BSA (manufactured by Wako Industry Co. Ltd.) and 2 mM EDTA (manufactured by Junsei Chemical Co., Ltd.), and then incubated in RPMI1640 (manufactured by Invitrogen) containing 5% BSA, 5 mM EDTA, 10 mM dithiothreitol (manufactured by Sigma-Aldrich) for 30 minutes, and an epithelial layer was removed. The large intestine tissue from which the epithelial layer was removed was washed twice with PBS containing 0.5% BSA and 2 mM EDTA and RPMI1640 containing 10 mM HEPES (manufactured by Sigma-Aldrich), and cut into a size of 3 to 5 mm. The cut large intestine pieces were digested using a lamina propria dissociation kit (manufactured by Miltenyi Biotec) and gentleMACS Dissociator (manufactured by Miltenyi Biotec). The cell specimen obtained by digestion was filtered through a 70 μm nylon mesh to obtain a suspension of single cells.

Cells isolated from the lung and intestine were treated with anti-CD16/32mAb (2.4G2; manufactured by Tonbo Biosciences) for 10 minutes on ice to avoid binding to FcγR, incubated with a combination of a monoclonal antibody against CD45.2, CD11b, CD38, NK1.1, DX5, B220, CD44, CD90.2, Sca-1, and RORγt and an anti-mouse DNAM-1 monoclonal antibody (Clone TX42, manufactured by BioLegend, Inc.) for 10 minutes, and then analyzed by flow cytometry. In place of the anti-mouse DNAM-1 monoclonal antibody, rat IgG2a (manufactured by BioLegend, Inc.) was used as an isotype control.

An innate lymphoid cell (ILC) subset 1 (ILC1) was identified as cells that are $CD45.2^+$, $CD11b^-$, $CD3E^-$, $NK1.1^+$, and $DX5^-$, an innate lymphoid cell (ILC) subset 2 (ILC2) was identified as cells that are $CD45.2^+$, $CD11b^-$, $B220^-$, $NK1.1^-$, $CD3E^-$, $CD44^+$, $CD90.2^+$, and $Sca\text{-}1^+$, and an innate lymphoid cell (ILC) subset 3 (ILC3) as cells that are $CD45.2^+$, $CD11b^-$, $B220^-$, $NK1.1^-$, $CD3E^-$, $CD44^+$, $CD90.2^+$, $ROR\gamma t^+$, and $Sca\text{-}1^-$.

The following antibodies were used.

Anti-CD11b (M1/70) monoclonal antibody: BD Biosciences

Anti-TCRβ monoclonal antibody (H57-597) and anti-Thy1.2 monoclonal antibody (53-2.1): BD PharMingen CD45.2 monoclonal antibody (104), anti-CD4 monoclonal antibody (RM4-5), anti-CD8 monoclonal antibody (53-6.7), and anti-CD127 monoclonal antibody (A7R34): BioLegend, Inc.

Anti-CD11c monoclonal antibody (N418): Tonbo biosciences

Anti-CD3ε monoclonal antibody (17A2): BioLegend, Inc.

Anti-NK1.1 monoclonal antibody (S17016D): BioLegend, Inc.

Anti-DX5 monoclonal antibody (DX5): BioLegend, Inc.

Anti-B220 monoclonal antibody (RA3-6B2): BioLegend, Inc.

Anti-CD44 monoclonal antibody (3/23): BioLegend, Inc.

Anti-CD90.2 monoclonal antibody (30-H12): BioLegend, Inc.

Anti-Sca-1 monoclonal antibody (E13-161.7): BioLegend, Inc.

Anti-RORγt monoclonal antibody (RORg2): BioLegend, Inc.

(Results)

The results are illustrated in FIGS. 13A and 13B. The dotted line indicates the isotype control, and the solid line indicates the case of using the anti-mouse DNAM-1 monoclonal antibody.

From FIGS. 13A and 13B, it was clear that DNAM-1 was expressed in ILC1, ILC2, and ILC3 in the lung and intestine.

[Analysis of Expression Level of Cytokines in ILCs]

(Method)

Wild-type (WT) mice (C57BL/6J) and DNAM-1 gene-deficient mice (hereinafter, also referred to as "DNAM-1KO") were intratracheally administered once with bleomycin hydrochloride (BLM, manufactured by Nippon Kayaku Co., Ltd.) dissolved in physiological saline at a dose of 6.5 mg/kg in a volume of 50 μL per mouse using an intratracheal nebulizer (manufactured by Natsume Seisakusho Co., Ltd.), thereby developing pulmonary fibrosis. ILCs ($CD45.2^+$, $CD11b^-$, $CD11c^-$, $TCR\beta^-$, $CD127^+$, and $Thy1.2^+$) present in the lung before and after administration of BLM were selected using BD FACSAria III (manufactured by BD Biosciences) and homogenized in Isogen reagent (manufactured by NIPPON GENE CO., LTD.). Thereafter, total RNA was isolated, and first-strand DNA was synthesized using High-Capacity cDNA Reverse Transcription Kit (manufactured by Thermo Fisher Scientific Inc.). Quantitative RT-PCR was performed using ABI 7500 Fast real-time PCR system and ABI Power SYBR Green PCR Master Mix (both manufactured by Thermo Fisher Scientific Inc.). The relative amount and copy number of gene transcripts were normalized as values for Actb transcripts.

(Results)

The results are illustrated in FIG. 14.

From FIG. 14, it was illustrated that the expression of IL17a, IL15, and IL13 mRNAs was decreased in ILCs of DNAM-1KO 3 days, 5 days, and/or 14 days after BLM administration compared to WT mice.

From these results, it was revealed that DNAM-1 was involved in cytokine production in ILCs.

[Expression of DNAM-1 in Human Peripheral Blood ILCs]

(Method)

Blood was collected from healthy volunteers, and peripheral blood mononuclear cells (PBMCs) were collected using Lymphoprep™ (manufactured by STEMCELL Technologies) according to the manufacturer's instructions. PBMCs were stained with conventional lineage markers (antibodies to CD3, CD4, CD8, CD19, CD14, CD16, CD11b, CD11c, CD56, and FcεRI), an anti-CD127 antibody, a CD45 antibody, and a humanized anti-DNAM-1 antibody (hTKB1). The expression of DNAM-1 was analyzed by flow cytometry on cells gated as total ILCs ($Lin^-$, $CD45^+$, and $CD127^+$). An antibody using human IgG1 (manufactured by BioLegend, Inc.) was defined as an isotype control instead of the humanized anti-DNAM-1 antibody (hTKB1).

(Results)

The results are illustrated in FIG. 15. The dotted line indicates the isotype control, and the solid line indicates the case of using the humanized anti-DNAM-1 antibody (hTKB1).

From FIG. 15, it was revealed that DNAM-1 was expressed in ILCs of human PBMCs. In addition, it was confirmed that hTKB1 can detect DNAM-1 on ILCs.

[Inhibition of Production of IFN-γ and TNF-α from ILCs by Anti-DNAM-1 Humanized Antibody]

(Method)

Blood was collected from healthy volunteers, and peripheral blood mononuclear cells (PBMCs) were collected using Lymphoprep™ (manufactured by STEMCELL Technologies) according to the manufacturer's instructions. $CD4^+$ T cells, $CD8^+$ T cells, and $CD56^+$ NK cells were removed from PBMCs using MACs LS column (manufactured by Miltenyi Biotec). 2 to $3\times10^6$ PBMCs from which T/NK cells were removed were cultured with 10 μg/mL of mouse IgG1, hAKB1-A, hAKB1-B, or hTKB1 in the presence of human IL-2 (5 ng/ml), human IL-12 (10 ng/ml), and human IL-15 (50 ng/ml) for 36 hours. Thereafter, the cells were stained with an antibody against lineage markers (Lin: CD3, CD4, CD8, CD19, CD14, CD16, CD11b, CD11c, and FcεRI), an anti-CD127 antibody, and an anti-CD45 antibody. ILCs ($Lin^-$, $CD127^+$, and $CD45^+$ cells) were selected using FACS Aria III (manufactured by BD Biosciences). Total RNA was isolated from the selected ILCs using Isogen reagent according to the manufacturer's protocol (manufactured by NIPPON GENE CO., LTD.). High-Capacity cDNA Reverse- Translcription Kit (manufactured by Applied Biosystems) was used for reverse transcription. Quantitative PCR analysis of Ifng was performed using ABI7500 sequence detector (manufactured by Applied Biosystems), Power SYBR Green PCR Master Mix (manufactured by Applied Biosystems), and primers shown below. To normalize the data, the expression level of Gapdh was measured as an internal standard.

```
Gapdh forward;
                                        (SEQ ID NO: 33)
5'-CTT CAC CAC CAT GGA GAA GGC-3'

Gapdh reverse;
                                        (SEQ ID NO: 34)
5'-GGC ATG GAC TGT GGT CAT GAG-3'

Ifng forward;
                                        (SEQ ID NO: 35)
5'-ACC AGA GCA TCC AAA AGA GTG T-3'

Ifng reverse;
                                        (SEQ ID NO: 36)
5'-TTA GCT GCT GGC GAC AGT TC-3'

Tnfa forward;
                                        (SEQ ID NO: 37)
5'-CAG CCT CTT CTC CTT CCT GAT-3'

Tnfa reverse;
                                        (SEQ ID NO: 38)
5'-GCC AGA GGG CTG ATT AGA GA-3'
```

(Results)

The results are illustrated in FIG. 16.

While mAKB1, which is a mouse monoclonal antibody, did not affect the expression of IFN-γ and TNF-α mRNAs, hAKB1-A, hAKB1-B, and hTKB1, which are humanized anti-DNAM-1 antibodies, inhibited the expression of IFN-γ and TNF-α mRNAs (FIG. 16).

SEQ ID NO 1: Amino acid sequence of HCDR1 of hTKB1, hAKB1-A, and hAKB1-B

SEQ ID NO 2: Amino acid sequence of HCDR2 of hTKB1, hAKB1-A, and hAKB1-B

SEQ ID NO 3: Amino acid sequence of HCDR3 of hTKB1, hAKB1-A, and hAKB1-B

SEQ ID NO 4: Amino acid sequence of LCDR1 of hTKB1, hAKB1-A, and hAKB1-B

SEQ ID NO 5: Amino acid sequence of LCDR2 of hTKB1, hAKB1-A, and hAKB1-B

SEQ ID NO 6: Amino acid sequence of LCDR3 of hTKB1, hAKB1-A, and hAKB1-B

SEQ ID NO: 7: Amino acid sequence of heavy chain variable region of mAKB1

SEQ ID NO: 8: Amino acid sequence of light chain variable region of mAKB1

SEQ ID NO: 9: Amino acid sequence of variable region of VH1 of hAKB1

SEQ ID NO: 10: Amino acid sequence of variable region of VH2 of hAKB1

SEQ ID NO: 11: Amino acid sequence of variable region of VL1 of hAKB1

SEQ ID NO: 12: Amino acid sequence of variable region of VL2 of hAKB1

SEQ ID NO: 13: Amino acid sequence of heavy chain of hAKB1-A (without signal peptide)

SEQ ID NO: 14: Amino acid sequence of heavy chain of hAKB1-B (without signal peptide)

SEQ ID NO: 15: Amino acid sequence of light chain of hAKB1-A and hAKB1-B (without signal peptide)

SEQ ID NO: 16: Amino acid sequence of heavy chain of hAKB1-A (with signal peptide)

SEQ ID NO: 17: Amino acid sequence of heavy chain of hAKB1-B (with signal peptide)
SEQ ID NO: 18: Amino acid sequence of light chain of hAKB1-A and hAKB1-B (with signal peptide)
SEQ ID NO: 19: Base sequence of heavy chain coding region of hAKB1-A
SEQ ID NO: 20: Base sequence of heavy chain coding region of hAKB1-B
SEQ ID NO: 21: Base sequence of light chain coding region of hAKB1-A and hAKB1-B
SEQ ID NO: 22: Amino acid sequence of heavy chain of hTKB1 (without signal peptide)
SEQ ID NO: 23: Amino acid sequence of light chain of hTKB1 (without signal peptide)
SEQ ID NO: 24: Amino acid sequence of heavy chain of hTKB1 (with signal peptide)
SEQ ID NO: 25: Amino acid sequence of light chain of hTKB1 (with signal peptide)
SEQ ID NO: 26: Base sequence of heavy chain coding region of hTKB1
SEQ ID NO: 27: Base sequence of light chain coding region of hTKB1
SEQ ID NO: 28: Amino acid sequence of signal peptide of hAKB1-A heavy chain
SEQ ID NO: 29: Amino acid sequence of signal peptide of hAKB1-B heavy chain
SEQ ID NO: 30: Amino acid sequence of signal peptide of hAKB1-A and hAKB1-B light chain
SEQ ID NO: 31: Amino acid sequence of signal peptide of heavy chain of hTKB1
SEQ ID NO: 32: Amino acid sequence of signal peptide of light chain of hTKB1
SEQ ID NO: 33: Base sequence of Gapdh forward primer
SEQ ID NO: 34: Base sequence of Gapdh reverse primer
SEQ ID NO: 35: Base sequence of Ifng forward primer
SEQ ID NO: 36: Base sequence of Ifng reverse primer
SEQ ID NO: 37: Base sequence of Infa forward primer
SEQ ID NO: 38: Base sequence of Infa reverse primer
SEQ ID NO: 39: Amino acid sequence of variable region of KU760971
SEQ ID NO: 40: Amino acid sequence of variable region of FJ039783

The invention claimed is:

1. A humanized anti-DNAM-1 antibody or an antigen-binding fragment thereof, comprising:

a heavy chain variable region comprising an HCDR1 having the amino acid sequence of SEQ ID NO: 1, an HCDR2 having the amino acid sequence of SEQ ID NO: 2, and an HCDR3 having the amino acid sequence of SEQ ID NO: 3, wherein the heavy chain variable region comprises an amino acid sequence at least 99% identical to SEQ ID NO: 10; and a light chain variable region comprising an LCDR1 having the amino acid sequence of SEQ ID NO: 4, an LCDR2 having the amino acid sequence of SEQ ID NO: 5, and an LCDR3 having the amino acid sequence of SEQ ID NO: 6, wherein the light chain variable region comprises an amino acid sequence at least 99% identical to SEQ ID NO: 11.

2. The humanized anti-DNAM-1 antibody or antigen-binding fragment thereof according to claim 1, wherein the light chain variable region comprises the amino acid sequence of SEQ ID NO: 11.

3. The humanized anti-DNAM-1 antibody or antigen-binding fragment thereof according to claim 2, wherein the heavy chain variable region comprises the amino acid sequence of SEQ ID NO: 10 and the light chain variable region comprises the amino acid sequence of SEQ ID NO: 11.

4. The humanized anti-DNAM-1 antibody or antigen-binding fragment thereof according to claim 2, wherein the heavy chain variable region comprises the amino acid sequence of SEQ ID NO: 9 and the light chain variable region comprises the amino acid sequence of SEQ ID NO: 11.

5. The humanized anti-DNAM-1 antibody according to claim 1, wherein the antibody comprises a heavy chain constant region of a class selected from the group consisting of: IgG, IgM, IgA, IgD, and IgE.

6. The humanized anti-DNAM-1 antibody according to claim 5, wherein the heavy chain constant region is a human IgG1 constant region.

7. The humanized anti-DNAM-1 antibody according to claim 6, wherein the human IgG1 constant region comprises one or more mutations that reduce an effector function.

8. The humanized anti-DNAM-1 antibody according to claim 7, wherein the one or more mutations comprise an amino acid A or F at each of amino acid positions 238 and 239 corresponding to the sequence of SEQ ID NO: 14.

9. The humanized anti-DNAM-1 antibody according to claim 7, wherein the one or more mutations comprise an amino acid A at each of amino acid positions 238 and 239 corresponding to the sequence of SEQ ID NO: 14.

10. The humanized anti-DNAM-1 antibody according to claim 1, comprising a heavy chain having an amino acid sequence at least 95% identical to SEQ ID NO: 14 and a light chain having an amino acid sequence at least 95% identical to SEQ ID NO: 15.

11. The humanized anti-DNAM-1 antibody according to claim 10, wherein the heavy chain comprises the amino acid sequence of SEQ ID NO: 14 and the light chain comprises the amino acid sequence of SEQ ID NO: 15.

12. A nucleic acid encoding the humanized anti-DNAM-1 antibody or antigen-binding fragment thereof according to claim 1.

13. A vector comprising the nucleic acid according to claim 12.

14. A host cell transfected with the vector according to claim 13.

15. A method of producing a humanized anti-DNAM-1 antibody or an antigen-binding fragment thereof, the method comprising culturing the host cell of claim 14 under conditions for expression of the humanized anti-DNAM-1 antibody or antigen-binding fragment thereof.

16. A method of inhibiting activation of an innate lymphoid cell in a subject, the method comprising administering to the subject an effective dose of the humanized anti-DNAM-1 antibody or antigen-binding fragment thereof according to claim 1.

17. A method of treating or preventing an inflammatory bowel disease, graft-versus-host disease, transplant rejection, an autoimmune disease, fibrotic disease, inflammatory enteritis, or an allergy, the method comprising administering to a patient in need thereof an effective dose of the humanized anti-DNAM-1 antibody or antigen-binding fragment thereof according to claim 1.

18. A method of treating an inflammatory bowel disease, the method comprising administering to a subject in need thereof an effective dose of the humanized anti-DNAM-1 antibody or antigen-binding fragment thereof according to claim 1.

19. The method of claim 18, wherein the inflammatory bowel disease is ulcerative colitis.

20. A method of treating an inflammatory bowel disease, the method comprising administering to a subject in need thereof an effective dose of the humanized anti-DNAM-1 antibody or antigen-binding fragment thereof according to claim 3.

21. A method of treating an inflammatory bowel disease, the method comprising administering to a subject in need thereof an effective dose of the humanized anti-DNAM-1 antibody or antigen-binding fragment thereof according to claim 11.

* * * * *